(12) United States Patent
Nagula et al.

(10) Patent No.: US 7,407,952 B2
(45) Date of Patent: *Aug. 5, 2008

(54) REVERSE-TURN MIMETICS AND COMPOSITIONS AND METHODS RELATED THERETO

(75) Inventors: Gangadhar Nagula, Nashha, NH (US);
Jan Urban, San Diego, CA (US);
Hwa-Ok Kim, Lexington, MA (US);
Christopher Lum, Kirkland, WA (US);
Hiroshi Nakanishi, San Diego, CA (US)

(73) Assignee: Myriad Genetics, Inc., Salt Lake City, UT (US)

( * ) Notice: Subject to any disclaimer, the term of this patent is extended or adjusted under 35 U.S.C. 154(b) by 205 days.

This patent is subject to a terminal disclaimer.

(21) Appl. No.: 11/175,920

(22) Filed: Jul. 6, 2005

(65) Prior Publication Data

US 2005/0245528 A1   Nov. 3, 2005

Related U.S. Application Data

(63) Continuation of application No. 10/268,062, filed on Oct. 9, 2002, now Pat. No. 6,943,157.

(60) Provisional application No. 60/328,296, filed on Oct. 9, 2001.

(51) Int. Cl.
*A61P 29/00* (2006.01)
*A61P 35/04* (2006.01)
*A61P 17/00* (2006.01)
*A61P 25/06* (2006.01)

(52) U.S. Cl. .................. 514/221; 514/249; 514/387

(58) Field of Classification Search ............... 514/221, 514/249, 387; 540/460, 501; 544/350; 435/6
See application file for complete search history.

(56) References Cited

U.S. PATENT DOCUMENTS

| 5,440,013 | A  | 8/1995 | Kahn |
| 5,545,568 | A  | 8/1996 | Ellman |
| 5,929,237 | A  | 7/1999 | Kahn |
| 6,013,458 | A  | 1/2000 | Kahn et al. |
| 6,184,223 | B1 | 2/2001 | Kahn et al. |
| 6,294,525 | B1 | 9/2001 | Stasiak et al. |
| 6,413,963 | B2 | 7/2002 | Kahn et al. |
| 6,440,955 | B1 | 8/2002 | Stasiak et al. |
| 6,943,157 | B2 | 9/2005 | Nagula et al. |

FOREIGN PATENT DOCUMENTS

| WO | WO 94/03494 | 2/1994 |
| WO | WO 97/15557 | 5/1997 |
| WO | WO 98/49168 | 11/1998 |
| WO | WO 01/00210 | 1/2001 |
| WO | WO 01/16135 | 3/2001 |

OTHER PUBLICATIONS

Abignente et al., "Research on heterocyclic compounds XVI. 2-Methylimidazo[1,2-a]pyrazine-3-carboxylic acids," *Chemical Abstracts Database*, Accession No. 103:87841, 1985.

Barrow and Sun, "Spiroquinazoline, a novel substance P inhibitor with a new carbon skeleton, isolated from *Aspergillus flavipes*," *Chemical Abstracts Databse*, Accession No. 121:129499, 1994.

Cutler et al., "Cinereain: a novel metabolite with plant growth regulating properties from *Botrytis cinerea*," *Chemical Abstracts Database*, Accession No. 109:165645, 1988.

Dennin et al., "Synthesis of derivatives of pyrazino[1,2-a]pyrimidin-4-ones," *Chemical Abstracts Database*, Accession No. 114:164135, 1991.

Faehnle and Rothe, "Syntheses and reactions of peptide cyclols," *Chemical Abstracts Database*, Accession No. 102:7061, 1985.

Gatta et al., "New [f]-fused xanthines: synthesis of 1,3-dipropyl-1H, 3H-pyrazino, pyrido, pyrimido and pyrrolo [2,1-f]purine-2, 4-diones,"*Chemical Abstracts Database:* 121:57444, 1994.

Hackh's Chemical Dictionary, Grant, Julius (ed.), pp. 332, 532 and 656, 1994.

Kadam et al., "Fermentative manufacture of multiple drug resistance-attenuating ardeemins," *Chemical Abstracts Marpat Database*, Accession No. 121:7435, 1994.

(Continued)

*Primary Examiner*—Bruck Kifle
(74) *Attorney, Agent, or Firm*—Herbert L. Ley, III; Jay Z. Zhang; Myriad IP Department

(57) ABSTRACT

Conformationally constrained compounds that mimic the secondary structure of reverse-turn regions of biologically active peptides and proteins having the following structure are disclosed:

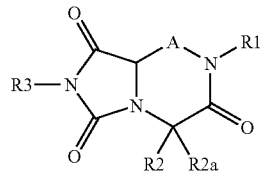

wherein A, $R_1$, $R_2$, $R_{2a}$ and $R_3$ are as defined herein. Such compounds have utility over a wide range of fields, including use as diagnostic and therapeutic agents. In particular, compounds of this invention are useful in pharmaceutical compositions as anti-inflammatory agents as well as inhibitors of central nervous disorders. Libraries containing the compounds of this invention are also disclosed, as well as methods for screening the same to identify biologically active members.

13 Claims, No Drawings

OTHER PUBLICATIONS

Kappe and Kappe, "Cross-conjugated and pseudo-cross-conjugated mesomeric betaines. XVIII. Bicyclic mesoionic pyrimidines with cardiovascular activity," *Chemical Abstracts Database*, Accession No. 116:83634, 1992.

Lam et al., "A new type of synthetic peptide library for identifying ligand-binding activity," *Nature* 354:82-84, 1991.

Lucente et al., "Synthesis and x-ray crystal structure of a tripeptidic cyclol," *Chemical Abstracts Database*, Accession No. 96:69410, 1982.

Lucente et al., "Cyclization of Activated N-Benzyloxycarbonyl-Tripeptides," *Tetrahedron Letters*, No. 11, pp. 1009-1012, 1978.

Numata et al., "Structures of cytotoxic substances and new quinazoline derivatives produced by a fungus from a salt water fish," *Chemical Abstracts Database*, Accession No. 116:210833, 1992.

Okawara et al., "Preparation and hydrogenolysis of fused piperazines by reaction of diamine and triamine derivatives with benzil. Applications to the synthesis of terminal N-monoprotected triamines," *Chemical Abstracts Database*, Accession No. 117:191810, 1992.

Okawara et al., "Simple preparation of terminal N-monoprotected triamines using fused piperazines," *Chemical Abstracts Database*, Accession No. 114:101300, 1991.

Penn et al., "Biosynthesis of glyantrypine by *Aspergillus clavatus*," *Chemical Abstracts Database*, Accession No. 117:44249, 1992.

Penn et al., "Glyantrypine, a novel anthranillic acid-containing metabolite of *Aspergillus clavatus*," *Chemical Abstracts Database*, Accession No. 117:127875, 1992.

Pinnen et al., "Cyclization under mild conditions of anthraniloyl and N-Methylanthraniloyl dipeptides,"*Chemical Abstracts Database*, Accession No. 110:76029, 1989.

Pinnen et al., "Ten-membered cyclotripeptides: influence of the ring-flexibility on intramolecular reactions," *Chemical Abstracts Database*, Accession No. 102:132448, 1985.

Rothe et al., "Cyclol formation during tripeptide cyclizations. Synthesis of a secondary cyclotripeptide, cyclo-(D-Phe-L-Pro-L-Pro)," *Chemical Abstracts Database*, Accession No. 97:56231, 1982.

Rothe et al., "Secondary all-L-cyclotripeptides," *Chemical Abstracts Database*, Accession No. 103:215766, 1985.

Sauter et al., "Novel basically substituted pyrimidines and benzothienopyrimidines," *Chemical Abstracts Database*, Accession No. 87:84931, 1977.

Tanaka and Narita, "Syntheses of pyrido[2,3-b]pyrazine derivatives," *Chemical Abstracts Database*, Accession No. 84:31002, 1976.

Vojkovsky et al., "Solid Phase Synthesis of Heterocycles Containing an 1-Acyl-3-oxopiperazine Skeleton," *J. Org. Chem.*, 63:3162-3163, 1998.

REVERSE-TURN MIMETICS AND COMPOSITIONS AND METHODS RELATED THERETO

CROSS-REFERENCE TO RELATED APPLICATIONS

This is a continuation of U.S. patent application Ser. No. 10/268,062, filed Oct. 9, 2002, which claims the benefit of U.S. Provisional Patent Application No. 60/328,296, filed Oct. 9, 2001; both of which are incorporated herein by reference in their entirety.

BACKGROUND OF THE INVENTION

1. Field of the Invention

The present invention relates generally to reverse-turn mimetics, including inhibitors of cell adhesion-mediated disease, central nervous system disorder, and several other disorders as well as to a chemical library of reverse-turn mimetics.

2. Description of the Related Art

Reverse-turns comprise one of three classes of protein secondary structure and display three (gamma-turn), four (beta-turns), or more (loops) amino acid side chains in a fixed spatial relationship to each other. Turns have proven important in molecular recognition events (Rose et al., *Advances in Protein Chemistry* 37:1-109, 1985) and have engendered a burgeoning field of research into small molecule mimetics of them (Hanessian et al., *Tetrahedron* 53:12789-12854, 1997). Many mimetics have either been external turn-mimetics which do not allow for the display of all the physiologically relevant side-chains (Freidinger et al., *Science* 210:656-8, 1980) or small, conformationally mobile cyclic peptide derivatives (Viles et al., *Eur. J. Biochem.* 242:352-62, 1996). However, non-peptide compounds have been developed which closely mimic the secondary structure of reverse-turns found in biologically active proteins or peptides. For example, U.S. Pat. Nos. 5,475,085, 5,670,155 and 5,672,681 to Kahn and published PCT WO94/03494 to Kahn all disclose conformationally constrained, non-peptidic compounds which mimic the three-dimensional structure of reverse-turns. More recently, U.S. Pat. No. 5,929,237 to Kahn, published PCT WO97/15577 to Kahn, published PCT WO98/49168 to Kahn et al., U.S. Pat. No. 6,013,458 to Kahn et al., U.S. Pat. No. 6,184,223 to Kahn et al. and published PCT WO01/16135A2 to Stasiak et al. disclosed additional, highly constrained bicyclic heterocycles as reverse-turn mimetics.

In view of the important biological role played by the reverse-turn, there is a need in the art for compounds that can mimic the reverse-turn structure. There is also a need in the art for methods of making stable reverse-turn mimetics, as well as the use of such stabilized structures to effect or modify biological recognition events that involve reverse-turn structures. The present invention fulfills these needs and provides further related advantages.

Cell adhesion is critical to the viability of living organisms. Adhesion holds multicellular tissues together and directs embryonic development. It plays important roles in wound healing, eradication of infection and blood coagulation. Integrins are a family of cell surface proteins intimately involved in all of these functions, and have been found in nearly every type of human cell except red blood cells. Abnormalities in integrin function contribute to a variety of disorders including inflammatory diseases, heart attack, stroke, and cancer. Integrins consist of heterodimers of $\alpha$ and $\beta$ subunits, non-covalently bound to each other. At least 15 different $\alpha$ and 9 different $\beta$ subunits are known. Integrin $\alpha_4\beta_1$ mediates cell adhesion primarily through binding to either vascular cell adhesion molecule-1 (VCAM-1) or an alternatively spliced variant of fibronectin containing the type III connecting segment (IIICS). Low molecular weight peptidyl derivatives have been produced as competitive inhibitors of $\alpha_4\beta_1$ and one has been shown to inhibit allergic airway responses in sheep (Lin et al., *J. Med. Chem.* 42:920-34, 1999).

Cyclic peptides and derivatives thereof that adopt reverse-turn conformations have proven to be inhibitors of VCAM-1 binding to $\alpha_4\beta_1$ (WO 96/00581; WO 96/06108; Doyle et al., *Int. J. Pept. Protein Res.* 47:427-36, 1996). In addition, a number of potent and selective (versus $\alpha_5\beta_1$) cyclic peptide-based inhibitors have been discovered (Jackson et al., *J. Med. Chem.* 40:3359-68, 1997). In addition, while $\alpha_4$ integrins appear to be down-regulated in carcinomas such as cervical and prostate, they appear to be up-regulated in metastatic melanoma (Sanders et al., *Cancer Invest.* 16:329-44, 1998), suggesting that inhibitors of $\alpha_4\beta_1$ and $\alpha_4\beta_7$ may be useful as anticancer agents. Several non-peptidyl beta-turn mimetics have also been reported to bind $\alpha_4\beta_1$ with $IC_{50}$s in the low micromolar range (Souers et al., *Bioorg. Med. Chem. Lett.* 8:2297-302, 1998). Numerous phenylalanine and tyrosine derivatives have also been disclosed as inhibitors of $\alpha_4\beta_1$ (WO 99/06390; WO 99/06431; WO 99/06433; WO 99/06434; WO 99/06435; WO 99/06436; WO 99/06437; WO 98/54207; WO 99/10312; WO 99/10313; WO 98/53814; WO 98/53817; WO 98/58902). However, no potent and orally available small molecule inhibitors have been disclosed.

The neuropeptide receptors for substance P (neurokinin-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (Pernow, *Pharmacol. Rev.*, 35:85-141, 1983). Substance P is also capable of producing both analgesia and hyperalgesia in animals, depending on dose and pain responsiveness of the animal (Frederickson et al., *Science* 199:1359, 1978; Oehme et al., *Science* 208:305, 1980) and plays a role in sensory transmission and pain perception (Jessell et al., *Advan. Biochem. Psychopharmacol.* 28:189, 1981). The usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Chrohn's disease, ocular injury and ocular inflammatory diseases, proliferative vitreo-retinopathy, irritable bowel syndrome and disorders of bladder function including cystitis and bladder detruser hyperreflexia have been reported (Maggi et al., *J. Auton. Pharmacol.* 13:23-93, 1993; Snider et al., *Chem. Ind.* 1:792-794, 1991).

It has furthermore been suggested that tachykinin receptor antagonists have utility in the following disorders: anxiety, depression, dysthymic disorders, chronic obstructive airways disease, hypersensitivity disorders such as poison ivy, vasospastic diseases such as angina and Reynauld's disease, fibrosing collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement of suppression such as systemic lupus erythmatosus (EPO Pub. No. 0,436,334), ophthalmic diseases such as conjunctivitis, vernal conjunctivitis, and the like, and cutaneous diseases such as contact dermatitis, atopic dermatitis, urticaria, and other eczematoid dermatitis (EPO Pub. No. 0,394,989).

The following documents relate to compounds that exhibit activity as neurokinin antagonists: U.S. Pat. Nos. 6,194,406 B1; 6,191,135 B1; 6,177,450 B1; 6,147,083; 6,114,315; 6,110,919; 6,063,926; 6,048,859; EPO Pub. No 1,099,446-A2; EPO Pub. No 1,110,958-A1; Published PCT WO200125219-A2; Published PCT WO200144200-A2.

While significant advances have been made in the synthesis and identification of conformationally constrained, reverse-turn mimetics, there is still a need in the art for small molecules that mimic the secondary structure of peptides. There is also a need in the art for libraries containing such members, particularly those small templates capable of supporting a high diversity of substituents. In addition, there is a need in the art for techniques for synthesizing these libraries and screening the library members against biological targets to identify bioactive library members. Further, there is a need in the art for small, orally available inhibitors of integrins, for use in treating inflammatory diseases and cardiovascular diseases, as well as some cancers. In particular there is a need for inhibitors of $\alpha_4\beta_1$ and $\alpha_4\beta_7$, for use in the treatment of rheumatoid arthritis, asthma, diabetes and inflammatory bowel disease. Further, there is a need in the art for small, orally available inhibitors of neurokinins, for use in treating inflammatory diseases, central nervous system disorders, as well as several other disorders. In particular there is a need for inhibitors of neurokinin-1, neurokinin-2, and neurokinin-3, for use in the treatment or prevention of various mammalian disease states, for example anxiety, asthma, cough, chronic obstructive pulmonary disease (COPD), bronchospasm, emesis, neurodegenerative disease, ocular disease, inflammatory diseases such as arthritis, central nervous system conditions such as migraine and epilepsy, nociception, psychosis, and various gastrointestinal disorders such as Crohn's disease.

The present invention fulfills these needs and provides further related advantages.

BRIEF SUMMARY OF THE INVENTION

In brief, the present invention is directed to conformationally constrained compounds that mimic the secondary structure of reverse-turn regions of biologically active peptides and proteins (also referred to herein as "reverse-turn mimetics"). The compounds of the present invention have the following general Structure (I):

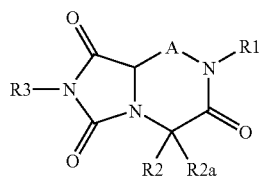

(I)

including pharmaceutically acceptable salts and stereoisomers thereof, wherein A, $R_1$ through $R_3$ are as defined below.

The present invention is also directed to libraries containing compounds of Structure (I), as well as methods for synthesizing such libraries and methods for screening the same to identify biologically active compounds. In addition, compositions containing a compound of this invention in combination with a pharmaceutically acceptable carrier are disclosed. Methods of use for treating cell-adhesion-mediated disease with the compounds of this invention and compositions comprising them are also disclosed. Further, methods of use for treatment and prevention of inflammatory and central nervous system disorders, as well as several other disorders with the compounds of this invention and compositions comprising them are also disclosed.

These and other aspects of this invention will be apparent upon reference to the following detailed description. To this end, various references are set forth herein which describe in more detail certain procedures, compounds and/or compositions, and are incorporated by reference in their entirety.

DETAILED DESCRIPTION OF THE INVENTION

The present invention is directed to reverse-turn mimetics and chemical libraries containing reverse-turn mimetics. The reverse-turn mimetics of the present invention are useful as bioactive agents, including (but not limited to) use as diagnostic, prophylactic and/or therapeutic agents, especially as anti-inflammatory agents, for central nervous system disorders, and as well as several other disorders. The reverse-turn mimetic libraries of this invention are useful in the identification of such bioactive agents. In the practice of the present invention, the libraries may contain from tens to hundreds to thousands (or greater) of individual reverse-turn mimetics (also referred to herein as "members").

In one aspect of the present invention, a reverse-turn mimetic is disclosed having the following Structure (I):

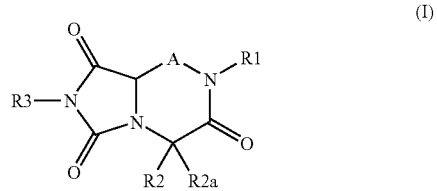

(I)

and pharmaceutically acceptable salts and stereoisomers thereof, wherein

A is —$(CR_4R_{4a})_m$— where m is 1, 2 or 3;

$R_2$ and $R_4$ are, at each occurrence, the same or different and independently an amino acid side chain moiety or amino acid side chain derivative;

$R_{2a}$ and $R_{4a}$ are, at each occurrence, the same or different and independently hydrogen, hydroxy, —COOH, —$CONH_2$, —$R_5$, —$OR_5$, —$COOR_5$, —$COR_5$ or —$CONHR_5$, where $R_5$ is lower alkyl optionally substituted with halogen or hydroxy; and $R_1$ and $R_3$ are the same or different and represent the remainder of the molecule.

As used herein, an "amino acid side chain moiety" refers to any amino acid side chain moiety present in naturally occurring alpha-amino acids and other "non-protein" amino acids commonly utilized by those in the peptide chemistry arts when preparing synthetic analogues of naturally occurring peptides, including D and L forms. The "non-protein" amino acids refer to unnatural alpha-amino acids, beta-amino acids and gamma-amino acids commonly utilized by those in the peptide chemistry arts when preparing synthetic analogues of naturally occurring peptides, including D and L forms. An "amino acid side chain moiety" as used herein, including (but not limited to) the naturally occurring amino acid side chain moieties are identified in Table 1 below. Other naturally occurring amino acid side chain moieties of this invention include (but are not limited to) the side chain moieties of 3,5-dibromotyrosine, 3,5-diiodotyrosine, hydroxylysine, γ-carboxyglutamate, phosphotyrosine, phosphothreonine and phosphoserine. In addition, glycosylated amino acid side chains may also be used in the practice of this invention, including (but not limited to) glycosylated threonine, serine, glutamine and asparagine.

TABLE 1

AMINO ACID SIDE CHAIN MOIETIES

| Amino Acid Side Chain Moiety | Amino Acid |
|---|---|
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_2$ | Lysine |
| —(CH$_2$)$_3$NHC(NH$_2$)NH$_2$ | Arginine |
| 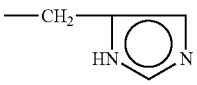 | Histidine |
| —CH$_2$COOH | Aspartic acid |
| —CH$_2$CH$_2$COOH | Glutamic acid |
| —CH$_2$CONH$_2$ | Asparagine |
| —CH$_2$CH$_2$CONH$_2$ | Glutamine |
| 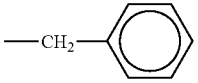 | Phenylalanine |
| 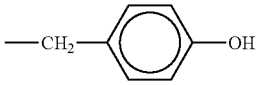 | Tyrosine |
| 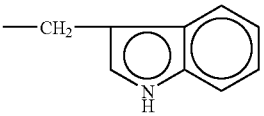 | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |
| 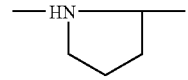 | Proline |
| 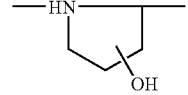 | Hydroxyproline |

In addition, as used herein, an "amino acid side chain derivative" represents modifications and/or variations to amino acid side chain moieties. For example, the amino acid side chain moieties of alanine, valine, leucine, isoleucine and phenylalanine may generally be classified as alkyl, aryl, or arylalkyl moieties, optionally substituted with one or more substituents as defined below. Accordingly, representative amino acid side chain derivatives include substituted or unsubstituted alkyl, aryl, arylalkyl, heterocycle, heterocyclealkyl, heteroaryl and heteroarylalkyl moieties. Examples of amino acid side chain derivatives include but not limited to hydroxylysine, homoserine, homotyrosine, homophenylalanine, citrulline, kynurenine, 4-aminophenylalanine, 3-(2-naphthyl)-alanine, 3-(1-naphthyl) alanine, methionine sulfone, t-butyl-alanine, t-butylglycine, 4-hydroxyphenylglycine, aminoalanine, phenylglycine, vinylalanine, prop argyl-glycine, 1,2,4-triazolo-3-alanine, 4,4,4-trifluoro-threonine, thyronine, 6-hydroxytryptophan, 5-hydroxytryptophan, 3-hydroxykynurenine, 3-aminotyrosine, trifuoromethyl-alanine, 2-thienylalanine, (2-(4-pyridyl)ethyl)cysteine, 3,4-dimethoxy-phenylalanine, 3,5-bis-trifluoromethyl-phenylalanine, 3,5-bistrifluoro-phenylalanine, 3-(2-thiazolyl)-alanine, ibotenic acid, 1-amino-1cyclopentane-carboxylic acid, 1-amino-1cyclohexanecarboxylic acid, quisqualic acid, 3-trifluoromethylphenylalanine, 4-trifluoromethylphenylalanine, cyclohexylalanine, cyclohexylglycine, thiohistidine, 3-methoxytyrosine, elastatinal, norleucine, norvaline, alloisoleucine, homoarginine, thioproline, dehydroproline, hydroxy-proline, isonipectotic acid, homoproline, cyclohexyl-glycine, α-amino-n-butyric acid, cyclohexylalanine, aminophenylbutyric acid, phenylalanines substituted at the ortho, meta, or para position of the phenyl moiety with one or two of the following: a (C$_1$-C$_4$) alkyl, a (C$_1$-C$_4$) alkoxy, halogen or nitro groups or substituted with a methylenedioxy group; β-2- and 3-thienylalanine, β-2- and 3-furanylalanine, β-2-, 3- and 4-pyridylalanine, β-(benzothienyl-2- and 3-yl) alanine, β-(1 and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-sulfo-tyrosine, 3-carboxy-tyrosine, 3-phospho-tyrosine, 4-methane sulfonic acid ester of tyrosine, 4-methane phosphonic acid ester of tyrosine, 3,5diiodotyrosine, 3-nitro-tyrosine, ε-alkyl lysine and δ-alkyl ornithine, and the like. Any of these "amino acid side chain derivative" maybe substituted with a methyl group at the alpha, beta or gamma positions, a halogen at any aromatic residue on the amino side chain, or an appropriate protective group at the O, N, or S atoms of the side chain moieties. Appropriate protective groups are disclosed in "Protective Groups In Organic Synthesis," T. W. Greene and P. G. M. Wuts, J. Wiley & Sons, NY, N.Y., 1991.

To this end, "alkyl" is a straight chain or branched, cyclic or noncyclic, saturated or unsaturated alkyl containing from 1 to 12 carbon atoms (also referred to herein as "C$_{1-12}$alkyl"). Similarly, a "lower alkyl" is as defined above, but contains from 1 to 4 carbon atoms (also referred to herein as a "C$_{1-4}$alkyl"). Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Representative unsaturated cyclic alkyls include cyclopentenyl and cyclohexenyl, and the like.

"Aryl" is an aromatic carbocyclic moiety contain from 6 to 12 carbon atoms (also referred to herein as a "C$_{6-12}$aryl"), such as phenyl and naphthyl.

"Arylalkyl" is an alkyl having at least one alkyl hydrogen atom replaced with an aryl moiety, such as benzyl, —(CH₂)₂phenyl, —(CH₂)₃phenyl, —CH(phenyl)₂, and the like.

Similarly, the amino acid side chain moieties of histidine, tryptophan, proline and hydroxyproline may generally be classified as heterocyclic or heterocyclicalkyl moieties, optionally substituted with one or more substituents as defined below. Accordingly, representative amino acid side chain derivatives also include substituted or unsubstituted heterocycle and heterocyclealkyl moieties.

As used herein, "heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Thus, in addition to the heteroaryls listed below, heterocycles also include morpholinyl, pyrrolidinonyl, pyrrolidinyl, piperidinyl, hydantoinyl, valerolactamyl, oxiranyl, oxetanyl, aziridinyl, azetidinyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle moiety, such as —CH₂(heterocycle), —(CH₂)₂(heterocycle), and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH₂pyridinyl, —CH₂pyrimidinyl, and the like.

The term "substituted" as used herein means any of the above groups—that is, alkyl, aryl, arylalkyl, heterocycle, heterocyclealkyl, heteroaryl or heteroarylalkyl—wherein at least one hydrogen atom is replaced with a substituent. In the case of an oxo substituent ("=O"), two hydrogen atoms are replaced. A "substituent" in this regard is halogen, oxo, hydroxy, haloalkyl (such as trifluoromethyl), —R, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —SO₂R, —NRSO₂R, —Si(R)₃, or —OP(OR)₃, wherein each occurrence of R is the same or different and independently hydrogen, alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocycle or a substituted heterocycle.

A "peptide" means at least two naturally or unnaturally occurring alpha-amino acids joined via a peptide bond. Depending upon the number of amino acids joined via peptide bonds, the resulting peptide may also be referred to as a "polypeptide" or "protein." Similarly, a "peptide derivative" means a peptide which has been covalently modified and/or which contains amino acids other than alpha-amino acids. Representative peptide derivatives include peptides which are N-alkylated, N-acylated or N-sulfonylated at the amino termini, with, for example, methyl, benzyl, acetyl, benzoyl, methanesulfonyl, phenylsulfonyl, allyloxycarbonyl, t-butyloxycarbonyl, benzyloxycarbonyl, or fluorenyloxycarbonyl moieties; peptides in which the carboxy termini are esterified (methyl, ethyl, benzyl) or reduced to a hydroxy or aldehyde; peptides which are N-alkylated at peptide bonds with, for example, methyl or 2-hydroxy-4-methoxybenzyl; and peptides which incorporate beta- or gamma-amino acids such as beta-alanine or gamma-aminobutyric acid.

A "linker" is any covalent bridging moiety that facilitates linkage of a compound of Structure (I), through the respective R₁, R₂, R₃ and/or R₄ moiety, to another moiety, agent, compound, solid support, molecule, amino acid, peptide or protein. For example, the compounds of this invention may be linked to one or more known compounds, such as biotin, for use in diagnostic or screening assays. Furthermore, one (or more) of R₁, R₂, R₃ or R₄ may be a linker joining the compound of Structure (I) to a solid support (such as a support used in solid phase peptide synthesis). Examples of such linkers include p-alkoxybenzyl alcohol, phenylacetamidomethyl, and 2-chlorotrityl chloride. In this context, linkage to another moiety or compound, or to a solid support, is preferable at the R₁ or R₃ position.

A "solid support" means any composition of matter to which another compound is attached directly or attached through a linker and which is insoluble in at least one solvent that the attached compound is soluble in. Alternatively, a "solid support" may be a composition of matter with similar solubility characteristics to the attached compound, but which may be readily precipitated from solution and filtered off as a solid. Representative examples include polystyrene, polyethylene glycol, polystyrene grafted with polyethylene glycol, polyacrylamide, polyamide-polyethylene glycol copolymer, controlled-pore glass, and silica.

The phrase "remainder of the molecule" means any moiety, agent, compound, solid support, molecule, linker, amino acid, peptide or protein covalently attached to the reverse-turn mimetic at either the R₁ and/or R₃ positions, including amino acid side chain moieties, amino acid side chain derivatives and peptide derivatives as defined above. Accordingly, an alternative depiction of Structure (I), the bond between the ring nitrogen atoms and the corresponding R₁ and R₃ moieties may be left undefined, as represented by the following Structures (I'):

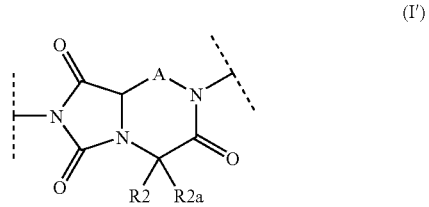

(I')

wherein "-----" represents the remainder of the molecule joined to the corresponding ring nitrogen through a covalent bond, and A and B are as defined above.

In an embodiment of Structure (I), $R_{2a}$ is hydrogen, and the compounds of this invention have the following Structure (II):

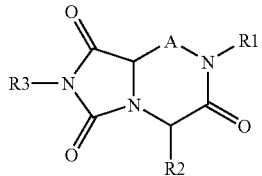

or pharmaceutically acceptable salts and stereoisomers thereof, wherein A, $R_1$, $R_2$ and $R_3$ are as defined above.

In an embodiment of Structure (II), each occurrence of $R_4$ and $R_{4a}$ are hydrogen, and the compounds of this invention have the following Structure (III):

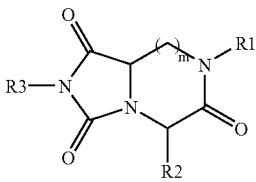

or pharmaceutically acceptable salts and stereoisomers thereof, wherein m, $R_1$, $R_2$ and $R_3$ are as defined above.

In a more specific embodiment of Structure (I), m is 2, A is —CH($R_4$)CH($R_4$)— and $R_{2a}$ is hydrogen, and the compounds of this invention have the following Structure (IV):

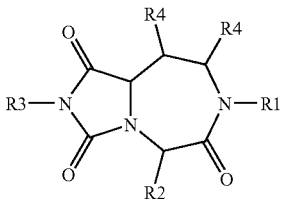

or pharmaceutically acceptable salts and stereoisomers thereof, wherein $R_1$, $R_2$ and $R_3$ and each occurrence of $R_4$ are as defined above.

In a more specific embodiment of Structure (IV), $R_4$ is hydrogen, and the compounds of this invention have the following Structure (V):

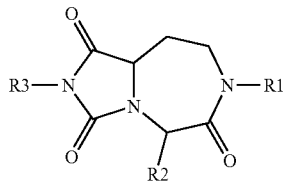

or pharmaceutically acceptable salts and stereoisomers thereof, wherein $R_1$, $R_2$ and $R_3$ are as defined above.

In a still more specific embodiment of Structure (I), m is 1, B is —CH($R_4$)—, $R_{2a}$ is hydrogens, and the compounds of this invention have the following structure (VI):

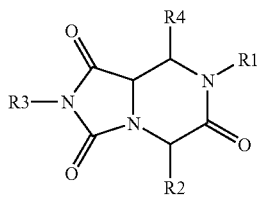

or pharmaceutically acceptable salts and stereoisomers thereof, wherein $R_1$, $R_2$, $R_3$ and $R_4$ are as defined above.

In a more specific embodiment of Structure (VI), $R_4$ is hydrogen, and the compounds of this invention have the following Structure (VII):

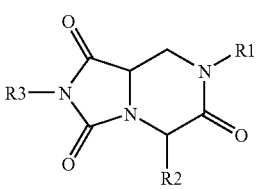

or pharmaceutically acceptable salts and stereoisomers thereof, wherein $R_1$, $R_2$ and $R_3$ are as defined above.

In a preferred embodiment of structure (I), $R_{2a}$ and each occurrence of $R_{4a}$ are hydrogens, $R_1$, $R_2$, $R_3$ and $R_4$ are the same or different and independently an amino acid side chain moiety or amino acid side chain derivative.

In Structure (I) above, a solid line designation for attachment of the various R groups to a carbon atom on the fused bicyclic ring indicates that these R groups may lie either above or below the plane of the page. If a reverse-turn mimetic of this invention is intended to mimic a reverse-turn of naturally occurring amino acids (i.e., "L-amino acids"), the R groups would generally lie below the plane of the page (i.e., "⋯⋯R") in Structure (I). However, if the reverse-turn mimetic of this invention is intended to mimic a reverse-turn containing one or more D-amino acids, then the corresponding R group or groups would lie above the plane of the page (i.e., "▬R") in Structure (I). Combinations of both the L- an D-amino acid forms are also included within the scope of this invention.

As mentioned above, the reverse-turn mimetics of the present invention are useful as bio-active agents, such as diagnostic, prophylactic, and therapeutic agents. The reverse-turn mimetics were found to effectively displace substance P in a calcium flux assay. The data thus indicate the ability of reverse-turn mimetics to antagonize neurokinin-1 and serve as potential therapy for central nervous system disorders and other disorders. Additionally, these reverse-turn mimetics were found to be effective in inhibiting binding of CSI peptide to $α_4β_1$ integrin. The compounds of this invention effectively antagonize cell adhesion and possess activity as anti-inflammatory agent.

In this invention, libraries containing reverse-turn mimetics of the present invention are disclosed. Once assembled, the libraries of the present invention may be screened to identify individual members having bioactivity. Such screening of the libraries for bioactive members may involve, for example, evaluating the binding activity of the members of the library or evaluating the effect the library members have on a functional assay. Screening is normally accomplished by contacting the library members (or a subset of library members) with a target of interest, such as, for example, an antibody, enzyme, receptor or cell line. Library members which are capable of interacting with the target of interest are referred to herein as "bioactive library members" or "bioactive mimetics". For example, a bioactive mimetic may be a library member which is capable of binding to an antibody or receptor, which is capable of inhibiting an enzyme, or which is capable of eliciting or antagonizing a functional response associated, for example, with a cell line. In other words, the screening of the libraries of the present invention determines which library members are capable of interacting with one or more biological targets of interest. Furthermore, when interaction does occur, the bioactive mimetic (or mimetics) may then be identified from the library members. The identification of a single (or limited number) of bioactive mimetic(s) from the library yields reverse-turn mimetics which are themselves biologically active, and thus useful as diagnostic, prophylactic or therapeutic agents, and may further be used to significantly advance identification of lead compounds in these fields.

Synthesis of the peptide mimetics of the library of the present invention may be accomplished using known peptide synthesis techniques, in combination with the component pieces of this invention. More specifically, any amino acid sequence may be added as any of the $R_1$, $R_2$, $R_3$ or $R_4$ moieties of the conformationally constrained reverse-turn mimetic. Preferably the amino acid sequence may be added as the $R_1$ or $R_3$ moieties. To this end, the mimetics may be synthesized on a solid support (such as polystyrene utilizing 4-hydroxymethylphenoxybutyrate as a linker) by known techniques (see, e.g., John M. Stewart and Janis D. Young, *Solid Phase Peptide Synthesis*, 1984, Pierce Chemical Comp., Rockford, Ill.; Atherton, E., Shepard, R. C. *Solid Phase Peptide Synthesis: A Practical Approach*; IRL: Oxford, 1989) or on a silyl-linked resin by alcohol attachment (Randolph et al., *J. Am. Chem. Soc.* 117:5712-14, 1995). The utility and easy of synthesis of the present invention is further exemplified by the applicability of wide variety of commercially available resins. To this end, core of either polystyrene or ArgoGel (polyethyleneglycol grafted polystyrene; Argonaut, San Carlos, Calif.) utilizing aminomethyl polystyrene, benzhydrylamine (BHA) methylbenzhydrylamine (MBHA) (Matsueda et al., *Peptides* 2:45, 1981), phenoxybenzylalcohol (Wang resin) (Wang *J. Am. Chem. Soc.* 95:1328, 1973), 2-clorotrytyl (Barlos et al., *Tetrahedron Lett.* 30:3943, 1989, ibid 30:3947, 1989), and PAL (Albericio et al., *J. Org. Chem.* 55:3730 1990) resins and other resins could be used in the synthesis of the present invention.

In addition, a combination of both solution and solid phase synthesis techniques may be utilized to synthesize the peptide mimetics of this invention. For example, a solid support may be utilized to synthesize the linear peptide sequence up to the point that the conformationally constrained reverse-turn is added to the sequence. A suitable conformationally constrained reverse-turn mimetic which has been previously synthesized by solution synthesis techniques may then be added as the next "amino acid" to the solid phase synthesis (i.e., the conformationally constrained reverse-turn mimetic, which has at least two reactive sites, may be utilized as the next residue to be added to the linear peptide). Upon incorporation of the conformationally constrained reverse-turn mimetic into the sequence, additional amino acids may then be added to complete the peptide bound to the solid support. Alternatively, the linear N-terminus and C-terminus protected peptide sequences may be synthesized on a solid support, removed from the support, and then coupled to the conformationally constrained reverse-turn mimetic in solution using known solution coupling techniques.

In this regard, the reverse-turn mimetics of the present invention may generally be prepared by sequential coupling of the individual component pieces either stepwise in solution or by solid phase synthesis illustrated in the following General Reaction Scheme. Such techniques are further illustrated in the Examples.

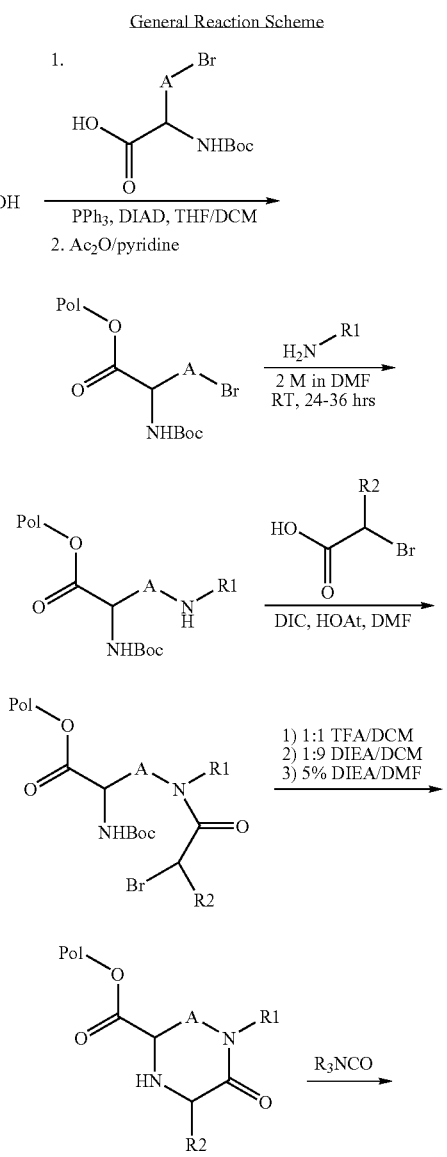

-continued

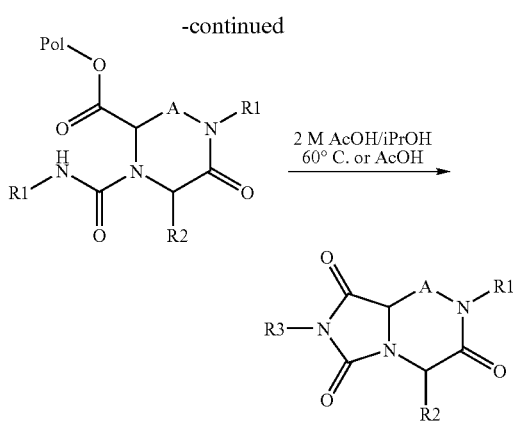

In another aspect of this invention, methods for constructing the libraries are disclosed. Traditional combinatorial chemistry (e.g., *The Combinatorial Index* Bunin, Academic Press, New York, 1998; Gallop et al., *J. Med. Chem.* 37:1233-1251, 1994) and parallel synthesis techniques permit a vast number of compounds to be rapidly prepared by the sequential combination of reagents to a basic molecular scaffold. For example, the above-disclosed synthesis may be carried out using the directed sorting technique of Nicolaou and coworkers. (Nicolaou et al., *Angew. Chem. Int'l. Ed.* 34:2289-2291, 1995). Presently, equipment for this technique is commercially available from IRORI (La Jolla, Calif.). Alternatively, the above disclosed synthesis may be carried out by parallel synthesis using a 48- or 96-well plate format wherein each well contains a fritted outlet for draining solvents and reagents (*A Practical Guide to Combinatorial Chemistry* Czarnik and DeWitt, Eds., American Chemical Society, Washington, D.C., 1997). Robbins (Sunnyvale, Calif.), Charybdis (Carlsbad, Calif.) and Bohdan (Chicago, Ill.) presently offer suitable equipment for this technique.

In a further aspect of this invention, methods for screening the libraries for bioactivity and isolating bioactive library members are disclosed. The libraries of the present invention may be screened for bioactivity by a variety of techniques and methods. Generally, the screening assay may be performed by (1) contacting a library with a biological target of interest, such as a receptor, and allowing binding to occur between the mimetics of the library and the target, and (2) detecting the binding event by an appropriate assay, such as by the colorimetric assay disclosed by Lam et al. (*Nature* 354:82-84, 1991) or Griminski et al. (*Biotechnology* 12:1008-1011, 1994). In a preferred embodiment, the library members are in solution and the target is immobilized on a solid phase. Alternatively, the library may be immobilized on a solid phase and may be probed by contacting it with the target in solution.

In another aspect, the present invention encompasses pharmaceutical compositions prepared for storage or administration that comprise a therapeutically effective amount of a compound of the present invention in a pharmaceutically acceptable carrier or diluent. Therapy with inhibitors of cell adhesion is indicated for the treatment and prevention of a variety of inflammatory conditions, particularly rheumatoid arthritis, inflammatory bowel disease and asthma. Those experienced in this field are readily aware of the circumstances requiring anti-inflammatory therapy.

The "therapeutically effective amount" of a compound of the present invention will depend on the route of administration, the type of warm-blooded animal being treated, and the physical characteristics of the specific animal under consideration. These factors and their relationship to determining this amount are well known to skilled practitioners in the medical arts. The "therapeutically effective amount" and the method of administration can be tailored to achieve optimal efficacy but will depend on such factors as weight, diet, concurrent medication and other factors that, as noted, those skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use, including diluents, are well known in the pharmaceutical art, and are described, for example, in *Remingtons Pharmaceutical Sciences*, Mack Publishing Co. (Gennaro Ed. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

Compounds of the present invention are useful for prevention and treatment of any condition in which an excess of integrin-mediated cell adhesion is a contributing factor. In particular, the compounds of the present invention are useful as agents for the prevention and treatment of inflammation. In the practice of the methods of this invention, a composition containing a therapeutically effective amount of a compound of this invention is administered to a warm-blooded animal in need thereof. For example, the compounds of this invention may be administered to a warm-blooded animal that has been diagnosed with, or is at risk of developing a condition selected from rheumatoid arthritis, atherosclerosis, Alzheimer's disease, AIDS dementia, ARDS, asthma, allergies, inflammatory bowel disease, CNS inflammation, atopic dermatitis, type I diabetes, encephalitis, myocardial ischemia, multiple sclerosis, meningitis, nephritis, reperfusion injury, restenosis, retinitis, psoriasis, stroke and tumor metastasis.

Multiple sclerosis (MS) is a progressively debilitating autoimmune disease of the central nervous system. Presently the exact antigen triggering the immune response is unknown. However, macrophages appear to attack and initiate the destruction of the fatty myelin sheaths surrounding nerve fibers in the brain. In an animal model of MS (experimental allergic encephalomyelitis) murine monoclonal antibodies to $\alpha_4\beta_1$ blocked adhesion of the leukocytes to the endothelium, and prevented inflammation of the central nervous system and subsequent paralysis of the animals (Yednock, Cannon et al., *Nature* 356: 63-6, 1992).

The compounds of the present invention are useful in the prevention and treatment of a wide variety of clinical conditions which are characterized by the presence of an excess tachykinin, in particular substance P, activity. These conditions may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, or example AIDS related neuropathy, diabetic neuropathy, chemotherapy-induced neuropathy, and other neuralgias; small cell carcinomas such as small cell lung cancer; respiratory diseases, particularly those associated with excess mucus secretion, such as chronic obstructive airways disease, bronchopneumonia, chronic bronchitis, acute bronchitis, diffuse panbronchilitis, emphysema, cystic fibrosis, asthma, and bronchospasm; airways disease modulated by neurogenic inflammation; laryngopharhngitis; bronchiectasis; conoisis; whooping cough; pulmonary tuberculosis; diseases associated with decreased glandular secretions, including lacrimation, such as Sjogren's syndrome, hyperlipoproteinemias IV and V, hemochromatosis, sarcoidosis, or amyloidosis; iritis; inflammatory diseases such as inflammatory bowel disease, inflammatory intestinal disease, psoriasis, fibrositis, ocular inflammation, osteoarthritis, rheumatoid arthritis, pruritis, and sunburn; hepatitis; allergies such eczema and rhinitis; hyper sensitivity disorders such as poison ivy; ophthalmic diseases such a conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; hemodialysis-associated itching; lichen planus; oedema, such as oedema caused by thermal injury; addiction disorders such as alcoholism; mental disease, particularly anxiety and depression; stress related somatic disorders; reflex sympathetic dystrophy such as shoulder/hand syndrome; dysthymic disorders; tenalgia attended to hyperlipidemia; postoperative neuroma, particularly of mastectomy; vulvar vestibulitis; amniogenesis; adverse immunological reactions such as rejection of transplanted tissues and disorders related to immune enhancement of suppression, such as systemic lupus erythmatosus; gastrointestinal (GI) disorders, including inflammatory disorders, and disease of the GI tract, such as gastritis, gastroduodenal ulcers, gastric carcinomas, gastric lymphomas, disorders associated with the neuronal control of viscera such as ulcerative colitis, Crohn's disease, irritable bowel syndrome, nausea, and emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness opioid analgesics, intoxication, resulting for example from consumption of alcohol, and variations in intercranial pressure, in particular, for example, drug or radiation induced emesis or post-operative nausea and vomiting; disorders of bladder function such as cystitis, bladder detrusor hyperreflexia, and incontinence; fibrosing and collagen diseases such as scleroderma and eosinophilic fascioliasis; disorders of blood flow caused by vasodilation and vasospastic diseases such as angina, migraine and Reynaud's disease; and pain of nociception, for example, chronic pain of that attributable to or associated with any of the foregoing conditions especially the transmission of pain in migraine, of such as headache, toothache, cancerous pain, back pain, and superficial pain on congelation, burn, herpes zoster of diabetic neuropathy. Hence, these compounds may be readily adapted to therapeutic use for the treatment of physiological disorders associated with an excessive stimulation of tachykinin receptors, especially neurokinin-1 and as neurokinin-1 antagonists in the control and/or treatment of any of the aforesaid clinical conditions in mammals, including humans.

The compounds of the present invention are also of value in the treatment of a combination of the above conditions, in particular in the treatment of combined post-operative pain and post-operative nausea and vomiting.

The compounds of the present invention are particularly useful in the treatment of nausea or emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure. Most especially, this compounds is of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulfonates and other compounds with an alkylating action such as nitrosoureas, cisplatin, and dacarbazine; antimetabolites, for example, folic acid, purine or pyrimidine antagonists; mitotic inhibitors, for example, vinca alkaloids and derivatives of podophyllotoxin; and cytotoxic antibiotics. Particular examples of chemotherapeutic agents are described, for example, D J Stewart in "Nausea and Vomiting: Recent Research and Clinical Advances", Eds. J. Kucharczyk et al., CRC Press Inc., Boca Raton, Fla., USA (1991), pages 177-203. Commonly used chemotherapeutic agents include cisplatin, dacarbazine, mechlorethamine, streptozocin, cyclophosphamide, carmustine, lomustine, doxorubicin, daunorubicin, procarbazine, mitomycin, cytarabine, etoposide, methotrexate, 5-fluorouracil, vinblastine, vincristine, bleomycin, and chlorambucil (Gralla et al., *Cancer Treatment Reports* 68, 163-172, 1984).

The compounds of the present invention are also of use in the treatment of emesis induced by radiation including radiation therapy such as in the treatment of cancer, or radiation sickness, and in the treatment of post-operative nausea and vomiting.

Further, the compounds of the present invention can act as calcium channel blocking agents. As such, the compounds of the present invention are useful in the prevention or treatment of clinical conditions that benefit from inhibition of the transfer of calcium ions across the plasma membrane of cells. These include diseases and disorders of the heart and vascular system such as angina pectoris, myocardial infarction, cardiac arrhythmia, cardiac hypertrophy, cardiac vasospasm, hypertension, cerebrovascular spasm and other ischemic disease. Furthermore, these compounds may be capable of lowering elevated intraocular pressure when administered topically to the hypertensive eye in solution in a suitable ophthalmic vehicle. Also, these compounds may be useful in the reversal of multidrug resistance in tumor cells by enhancing the efficacy of chemotherapeutic agents. In addition, the compounds may have activity in blocking calcium channels in insect brain membranes and so may be useful as insecticides.

The compounds of the present invention are particularly useful in the treatment of pain or nociception and/or inflammation and disorders associated therewith such as, for example: neuropathy, such as diabetic or peripheral neuropathy and chemotherapy-induced neuropathy; postherpetic and other neuralgias; asthma; osteoarthritis; rheumatoid arthritis; and especially migraine. The compounds of the present invention are also particularly useful in the treatment of diseases characterized by neurogenic mucus secretion, especially cystic fibrosis.

The compounds of the present invention may be used singularly, as a combination of two or more compounds, in combination with other known inhibitors of inflammation, in combination with other known inhibitors of central nervous disorders, or in combination with known inhibitors of other disorders. For example the compounds of this invention may be used therapeutically with corticosteroids, non-steroidal anti-inflammatory agents, COX-2 inhibitors, matrix metalloprotease inhibitors or lipoxygenase inhibitors. The compounds of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, intranasal, intrarectal or intramuscular form, all using forms well known to those of ordinary skill in the pharmaceutical arts. The compounds may be administered intraocularly or topically as well as orally or parenterally.

The compounds of this invention may be administered by inhalation, and thus may be delivered in the form of an aerosol spray from pressurized packs or nebulizers. The compounds may also be delivered as powders which may be formulated and the powder composition may be inhaled with the aid of an insufflation powder inhaler device. A preferred delivery system for inhalation is the metered dose inhalation aerosol, which may be formulated as a suspension or solution of a compound of the invention in suitable propellants, such as fluorocarbons or hydrocarbons. Another preferred delivery system is the dry powder inhalation aerosol, which may be formulated as a dry powder of a compound of this invention with or without additional excipients.

The compounds of the invention can be administered in the form of a depot injection or implant preparation that may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of this invention may also be delivered by the use of monoclonal antibodies as individual carriers to which the compound molecules are coupled. The integrin or neurokinin inhibitors may also be coupled with soluble polymers as targetable drug carriers. Such polymers can include polyvinlypyrrolidone, pyran copolymer, polyhydroxy-propyl-methacrylamide-phenol, polyhydroxyethyl-aspartarnide-phenol, or polyethyleneoxide-polylysine substituted with palmitoyl residues. Furthermore, the integrin or neurokinin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The pharmaceutical compositions of this invention may be used in the form of a pharmaceutical preparation, for example in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparation, in solid, semisolid, or liquid form, and in addition auxiliary, stabilizing, thickening and coloring agents and perfumes may be used. The active object compounds is included in the pharmaceutical composition in an amount sufficient to produce the desired effect upon the process or condition of the disease.

For preparing solid compositions such as tablets, the principal active ingredient is mixed with a pharmaceutical carrier; conventional tableting ingredients such as corn starch, lactose, sucrose, sorbitol, talc, stearic acid, magnesium stearate, dicalcium phosphate or gums, and other pharmaceutical diluents; water, to from a solid preformulation composition containing homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type, described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers coatings, such materials including a number of polymeric acids and mixtures of polymeric acids with such materials as shellac, acetyl alcohol and cellulose acetate.

The liquid forms in which the compositions of the present invention may be incorporated for administration orally or by injection include aqueous solution, suitably flavored syrups, aqueous or oil suspensions, and emulsions with acceptable oils such as cottonseed oil, sesame oil, coconut oil or peanut oil, or with solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation of insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly form the nebulizing device or the nebulizing device may be attached to a face mask, tent or intermittent positive pressure breathing machine. Solution, suspension or powder compositions may be administered, preferably orally of nasally, from devices which deliver the formulation in an appropriate manner.

For the treatment of the clinical conditions and diseases noted above, the compounds of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of certain conditions it may be desirable to employ a compound of the present invention in conjunction with another pharmacologically active agent. For example, a compound of the present invention may be presented together with another therapeutic agent as a combined preparation for simultaneous, separate, or sequential use for the relief of emesis. Such combined preparations may be, for example, in the form of a twin pack. A preferred combination comprises a compound of the present invention with a chemotherapeutic agent such as an alkylating agent, antimetabolite, mitotic inhibitor, or cytotoxic antibiotic, as described above. In general, the currently available dosage forms of the known therapeutic agents for use in such combinations will be suitable.

Similarly, for the treatment of respiratory diseases, such as asthma, a compound of the present invention may be used in conjunction with a bronchodilator, such as a $\beta_2$-adrenergic receptor agonist of a tachykinin antagonist which acts at neurokinin-2 receptors. Also, for the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis, a compound of the present invention may be used in conjunction with a tachykinin antagonist which acts at neurokinin-2 receptors, or with tachykinin receptor antagonist which acts at neurokinin-1, neurokinin-2, and neurokinin-3 receptors. Similarly, for the prevention of treatment of emesis a compound of the present invention may be used in conjunction with other anti-emetic agents, especially $5HT_3$ receptor antagonists, such as ondansetron, granisetron, tropisetron, decadron, zatisetron, as well as other commercially and naturally available pharmacologically active agents. Likewise, for the prevention or treatment of migraine a compound of the present invention may be used in conjunction with other anti-migraine agents, such as ergotamines or $5HT_3$ agonists, especially sumatriptan. Likewise, for the treatment of behavioral hyperalgesia, a compound of the present invention may be used in conjunction with an antagonist of N-methyl D-asparatate (NMDA), such as dizocilpine. For the prevention of treatment of inflammatory conditions in the lower urinary tract, especially cystitis, a compound of the present invention may be used in conjunction with an antiinflammatory agent, such as a bradykinin receptor antagonist. The compound of the present invention and the other pharmacologically active agent may be administered to a patient simultaneously, sequentially or in combination.

The compounds of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication of special diets then being followed by patient, and other factors which those skilled in the art will recognize, with the appropriate dosage ultimately being at the discretion of the attendant physician.

In the treatment of a condition associated with an excess of tachykinins, an appropriate dosage level will generally be about 0.001 to 50 mg per kg patient body weight per day which may be administered in single or multiple doses. Preferably, the dosage level will be about 0.01 to about 25 mg/kg per day; more preferably about 0.05 to about 10 mg/kg per day. For example, in the treatment of conditions involving the neurotransmission of pain sensations, a suitable dosage level is about 0.001 to 25 mg/kg per day, preferably about 0.05 to 10 mg/kg per day, and especially about 0.1 to 5 mg/kg per day. A compound may be administered on a regimen of 1 to 4 times per day, preferably once or twice per day. In the treatment of emesis using an injectable formulation, a suitable dosage level is about 0.001 to 10 mg/kg per day, preferably about 0.005 to 5 mg/kg per day, and especially about 0.05 to 5 mg/kg per day. A compound may be administered on a regiment of 1 to 4 times per day, preferably once or twice per day.

The dose and method of administration can be tailored to achieve optimal efficacy but will depend on such factors as weight, diet, concurrent medication and other factors that those skilled in the medical arts will recognize. When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions.

The following examples are provided for purposes of illustration, not limitation. These examples illustrate the syntheses of reverse-turn mimetics of this invention. Specifically, the preparation of reverse-turn mimetics was carried out on solid phase. The solid phase syntheses of these reverse-turn mimetics demonstrate that libraries containing such members may be readily prepared.

TABLE 2

| Abbreviations used in Examples | |
|---|---|
| Reagents: | |
| AcOH | acetic acid |
| Ac$_2$OH | acetic anhydride |
| BOP | benzotriazol-1-yloxy-tris(dimethylamino)phosphonium hexafluorophosphate |
| DIAD | diisoproppyl azodicarboxylate |
| DIC | diisopropyl carbonyl diimide |
| DIEA | N,N-diisopropylethylamine |
| HATU | O-(7-azabenzotriazol-l-yl)-1,1,3,3-tetramethyluronium hexafluorophosphate |
| HOAt | 1-hydroxy-7-azabenzotriazole |
| HOBt | 1-hydroxybenzotriazole hydrate |
| MCPBA | 3-chloroperoxybenzoic acid |
| PyBOP | benzotriazol-1-yloxy-tris(pyrrolidino)phosphonium hexafluorophosphate |
| TFA | trifluoroacetic acid |
| TPP | triphenylphosphine |
| Solvents: | |
| ACN | acetonitrile |
| DCM | dichloromethane |
| DMF | dimethylformamide |
| DMSO | dimethylsulfoxide |
| Et$_2$O | diethyl ether |

TABLE 2-continued

Abbreviations used in Examples

| | |
|---|---|
| MeOH | methanol |
| THF | tetrahydrofuran |
| Protecting Groups: | |
| All | allyl |
| Alloc | allyloxy carbonyl |
| Fmoc | 9-fluorenylmethoxy carbonyl |
| tButyl | tertiary-Butyl |
| Trt | triphenylmethyl |
| Others: | |
| Dess-Martin | Dess-Martin periodinane |
| LC/MS | HPLC/Mass spectrometry |
| rt | room temperature |

The reactions were carried out in but not limited to the following: plastic disposable syringes of the appropriate size, each fitted with a polypropylene frit to retain the resin, 1-10 ml reaction vessel compatible with Symphony Automated Peptide Synthesizer (Protein Technologies), ACT 90 Synthesizer (Advanced ChemTech), Robbins block, or IRORI system.

LCMS analysis was performed on reverse-phase $C_{18}$ Zorbax columns using the following solvent system: A, water with 0.1% formic acid; B, acetonitrile with 0.1% formic acid. The following conditions were applied: column 2.1×30 mm, 5-95% B in 3 min, flow 0.8 ml/min. Mass spectra for separated peaks were obtained by electrospray (ES) using a MicroMass LCZ mass spectrometer.

EXAMPLES

These examples illustrate the synthesis of representative reverse-turn mimetics of this invention. The solid phase syntheses of these reverse-turn mimetics demonstrate that libraries containing such members may be readily prepared. Structures of representative reverse-turn mimetics are given in Table 3. These examples illustrate the syntheses of reverse-turn mimetics of this invention.

Example 1

Synthesis of Component Pieces

In this example, the synthesis of representative component pieces which may be combined to form the reverse-turn mimetic of the present invention is disclosed.

A. Representative First Component Piece

A first component piece having the following structure 1 was synthesis:

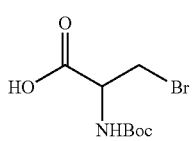

Structure 1

The synthesis of the representative first component piece is depicted schematically below.

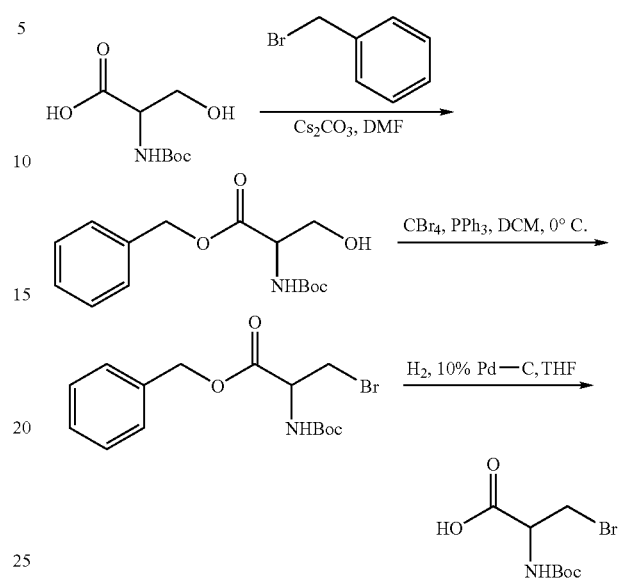

In a round-bottomed flask were placed N-BocSerine (20.0 g, 89.605 mmol, 1 eq.), benzyl bromide (10.76 ml, 90.50 mmol, 1.01 eq.) and cesium carbonate (56.64 g, 173.84 mmol, 1.94 eq.) in DMF (180 mL). The suspension was stirred under nitrogen at room temperature for 2 hrs to overnight. The mixture was partitioned between water and ethyl acetate (1:1, 1000 ml) and aqueous layer was re-extracted with ethyl acetate (2×200 mL). The combined organic layers were washed with water (2×500 mL), saturated sodium chloride, and dried over sodium sulfate. The solvents were removed in vacuo and the crude material purified on silica gel to get N-Boc-serine benzyl ester.

The N-Boc-serine benzyl ester was brought up in dichloromethane (170 mL) and treated with carbon tetrabromide (26.37 g, 79.51 mmol, 1.2 eq.), and triphenylphosphine (25.20 g, 96.08 mmol, 1.45 eq.) and the solution was stirred at 0° C. for 30 min. The volatiles were then evaporated in vacuo and the residue was triturated with ether (1000 mL). The solid that separated out was filtered off and organic layer was evaporated in vacuo to get the crude product. The crude material was purified by flash chromatography on silica gel to get N-Boc-β-bromoalanine benzyl ester.

The N-Boc-β-bromoalanine benzyl ester (22.0 g, 61.41 mmoles) was dissolved in tetrahydrofuran (160-180 mL) and treated with 10% Pd—C (10-15% w/w). The suspension was stirred under hydrogen atmosphere overnight. The mixture was filtered and the solvents removed to afford ~17.0 g of the Boc-β-bromoalanine free acid.

B. Representative Second Component Piece

A second component piece having the following structure 2 was synthesized:

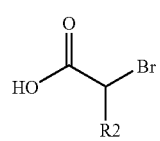

Structure 2

The synthesis of the representative second component piece is depicted schematically below.

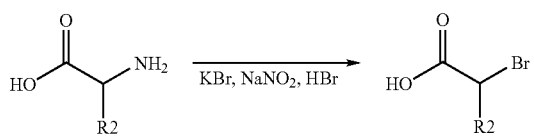

Potassiumbromide (3.7 eq) was weighed out into a three neck round bottom flask and 4.4 eq. of 0.75M aq. HBr was added into it. Sodiumnitrite (1.9 eq) was added in one portion followed by free aminoacid (1 eq.) in portions maintaining the temperature at −4 to −7° C. and reaction was then continued at the above temperature for the next 1.5 hr. The reaction mixture was diluted with water and extracted with cold EtOAc (2×100 ml) that has been cooled to 0° C. The combined organic layers were washed with brine solution, dried over Na$_2$SO$_4$ and concentrated in vacuo to get the crude product, which was purified using flash chromatography on silica gel or otherwise used as such.

C. Representative Third Component Piece

A third component piece having the following structure 3 was synthesized:

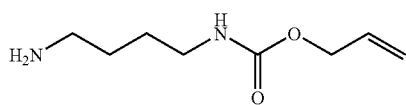

The synthesis of the representative third component piece is depicted schematically below.

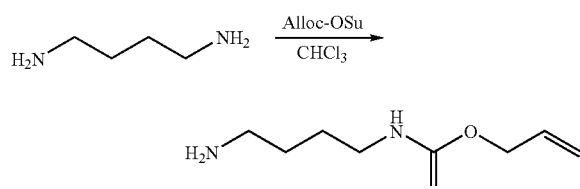

To the solution of 1,4-diamono butane (20.0 g, 5 equivalents) in CHCl$_3$ (200 ml) taken in a three neck round bottom flask, solution of Alloc-Osu (11.75 g, 1 equivalent) in CHCl$_3$ (200 ml) was added drop wise using pressure equalizing dropping funnel at 0° C. over a period of 1 hr. The reaction then allowed to come to RT and continued for overnight. Then the solid compound, which was insoluble in chloroform was filtered off. The organic layer evaporated in vacuo. To the residue was added saline water (use minimum amount) and filtered through the sintered funnel to remove the undissolved N-dialloc-1,4-diaminobutane. The aqueous layer was then extracted with ether (2×300 ml) and dried on Na$_2$SO$_4$. The ether solution was then filtered and evaporated in vacuo to get the N-alloc-1,4-diaminobutane as liquid. The final liquid compound was dried under vacuum for overnight.

D. Representative Forth Component Piece

A forth component piece having the following structure 4 was synthesized:

The synthesis of the representative forth component piece is depicted schematically below.

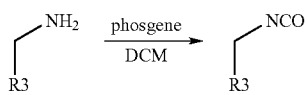

To a solution of amine (3.38 g, 1 eq) in DCM (50 ml), saturated NaHCO$_3$ (50ml) was added followed by 2M solution of phosgene in toluene (1.2-10 eq) at 0° C. The reaction was continued for 30-45 min at 0° C. to RT. The organic layer was collected and the aqueous layer was extracted with DCM (×2). The combined organic layers were dried over Na$_2$SO$_4$ and solvents were evaporated in vacuo to get crude isocyanate, which was used as such without any purification.

Example 2

Synthesis of Representative Reverse-Turn Mimetic

These examples illustrate the synthesis of representative reverse-turn mimetics of this invention. Specifically, the preparation of [3.4.0] bicyclic reverse-turn mimetics was carried out on solid phase.

Representative compounds of this invention were synthesized according to the following procedure. The following reactions were generally performed in 2.5 mL polyethylene syringes fitted with fritted filters to allow easy washing of the resin:

Method A:

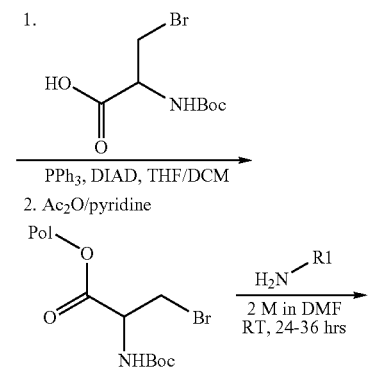

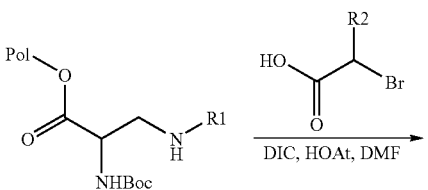

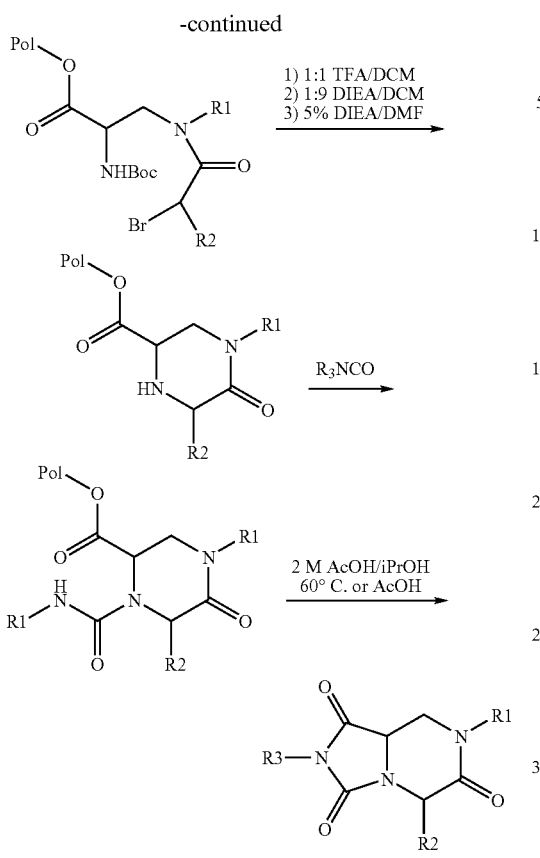

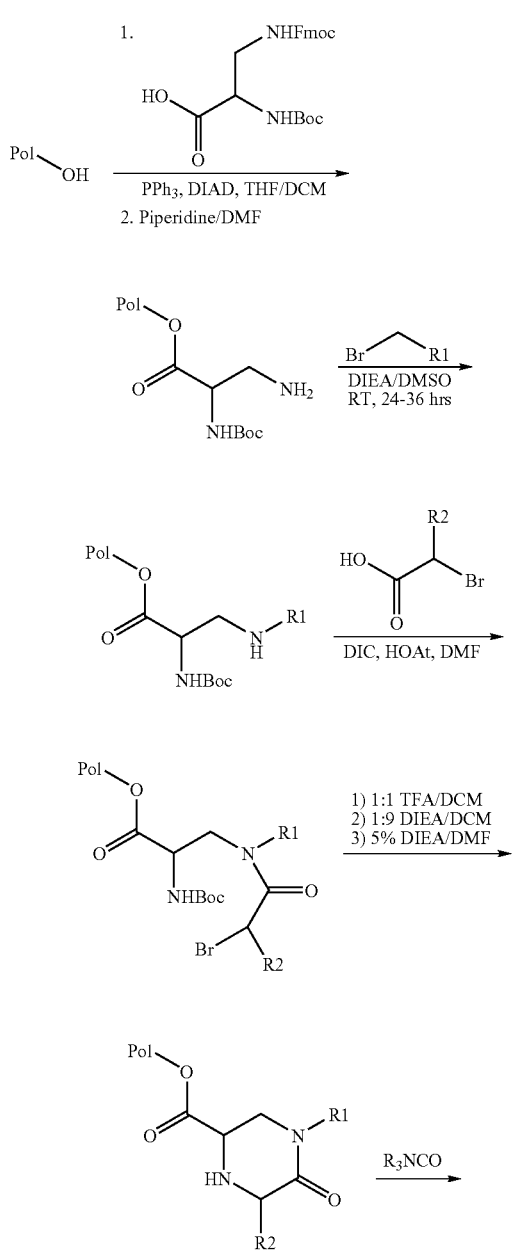

In general, a batch of hydroxymethyl polystyrene resin (1 eq.) stirred at 0° C. in 2:1 THF:dichloromethane (20 mL/g) was treated with N-Boc-β-bromoalanine (3 eq.), triphenylphosphine (3 eq.), and diisopropyldiazodicarboxylate (DIAD) (3 eq.). The reaction was allowed to come to room temperature and then stirred overnight. The resin was filtered and washed with DCM, DMF, MeOH, DCM and Et$_2$O and dried under vacuum. The resin was then contacted with acetic anhydride (1.2 eq.) and pyridine (1.2 eq.) in DCM. The resin was filtered and washed with DCM, DMF, MeOH, DCM and dried under vacuum.

The resin was then treated with a 2M solution of the R$_1$—NH$_2$ in dimethylformamide (DMF) and stirred overnight at room temperature or 60° C. The resin was filtered and washed with, DMF, methanol and DCM and dried under vacuum. The substitution value was determined by reaction of a small portion of resin with 0.5M FmocCl/0.5M diisopropylethylamine (DIEA) in DCM followed treatment with 1:3 piperidine/DMF and measurement of the absorbance of solution at 301 nm.

The resin was then treated with a DMF solution of the R$_2$-α-bromo acid (Soueres et al., Synthesis 4:583-585, 1999) (0.1N), diisopropylcarbodiimide (DIC) (0.1N) and 1-hydroxyazabenzotriazole (HOAt) (0.1N) for 5h to overnight, until chloranil test (acetaldehyde/chloranil/DMF) was negative (no blue color on resin). The resin was filtered and washed with DMF, DCM and Et$_2$O and treated with 1:1 trifluoroacetic acid (TFA)/DCM for 30 min followed by washing with DCM and Et$_2$O then washed with 1:9 DIEA/DMF. Cyclization of the ketopiperazine ring was effected using DMF or DMSO or 5% DIEA/DMF for 5 h to overnight at room temperature or 60° C. or until kaiser test was negative. The resin was washed with DMF, MeOH and DCM and dried.

The resin was then treated with R$_3$-isocyanate (5 eq.) in DCM for 3 h to overnight until chloranil test was negative. The resin was filtered and washed with DCM, DMF, DCM and dried under vacuum. The dried resin was then treated with 2M acetic acid in isopropanol or glacial acetic acid at 60° C. overnight. The resin was filtered and the resin washed once with isopropanol or acetic acid. The combined filtrates were frozen to −76° C. and the solvent removed in vacuo or lyophilized.

Method B:

-continued

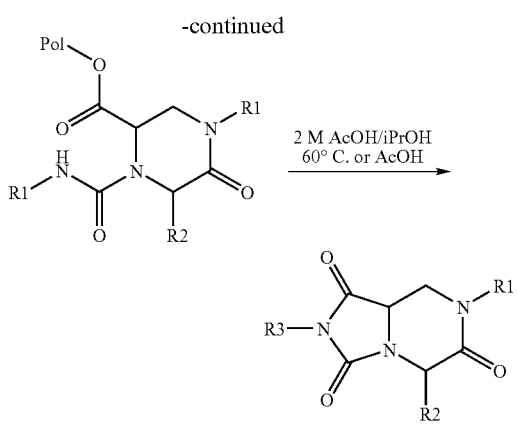

2 M AcOH/iPrOH
60° C. or AcOH

In general, a batch of hydroxymethyl polystyrene resin (1 eq.) stirred at 0° C. in 2:1 THF/DCM (20 mL/g) was treated with α-N-Boc-β-N-Fmoc (3 eq.), triphenylphosphine (3 eq.), and diisopropyldiazodicarboxylate (DIAD) (3 eq.). The reaction was allowed to come to room temperature and then stirred overnight. The resin was filtered and washed with DCM, DMF, MeOH, DCM and Et$_2$O and dried under vacuum. The resin was then contacted with acetic anhydride (1.2 eq.) and pyridine (1.2 eq.) in DCM. The resin was filtered and washed with DCM, DMF, MeOH, DCM and dried under vacuum. This resin was then treated with a 25% solution of the piperidine in dimethylformamide (DMF) and stirred for 10 min at room temperature. The resin was filtered and washed with, DMF, MeOH, DCM and DMSO.

Resin was treated with solution of appropriate alkyl bromide, Br—R$_3$, (4 eq) and diisopropylethylamine (DIEA) (6 eq.) in DMSO. The reaction was let to proceed at room temperature for 2-4 hours (Completion of reaction was checked by Kaiser test). The resin was filtered and washed with DMSO, DMF, and DCM.

The resin was then treated with a DMF solution of the R$_2$-α-bromo acid (Soueres et al., *Synthesis* 4:583-585, 1999) (0.1N), diisopropylcarbodiimide (DIC) (0.1N) and 1-hydroxyazabenzotriazole (HOAt) (0.1N) for 5 h to overnight, until chloranil test (acetaldehyde/chloranil/DMF) was negative (no blue color on resin). The resin was filtered and washed with DMF, DCM and Et$_2$O and treated with 1:1 trifluoroacetic acid (TFA)/DCM for 30 min followed by washing with DCM and Et$_2$O then washed with 1:9 DIEA/DMF. Cyclization of the ketopiperazine ring was effected using DMF or DMSO or 5% DIEA/DMF for 5 h to overnight at room temperature or 60° C. or until kaiser test was negative. The resin was washed with DMF, MeOH and DCM and dried.

The resin was then treated with R$_3$-isocyanate (5 eq.) in DCM for 3 h to overnight until chloranil test was negative. The resin was filtered and washed with DCM, DMF, DCM and dried under vacuum. The dried resin was then treated with 2M acetic acid in isopropanol or glacial acetic acid at 60° C. overnight. The resin was filtered and the resin washed once with isopropanol or acetic acid. The combined filtrates were frozen to −76° C. and the solvent removed in vacuo or lyophilized.

Example 3

Representative Compounds of Structure Type (VI)

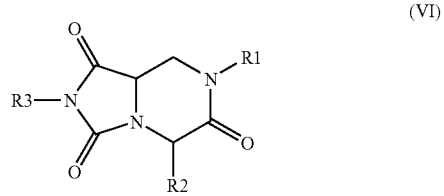

(VI)

Representative compounds of this invention were synthesized according to the procedures set forth in Examples 2.

TABLE 3

Representative Compounds

| Cpd | R1 | R2 | R3 | Method* | LC RT | (M + H)$^+$ |
|---|---|---|---|---|---|---|
| 1 | benzyl-X$_1$ | X$_2$ | X$_3$-CH$_2$CH$_2$-phenyl | A | 1.00 | 378.5 |
| 2 | benzyl-X$_1$ | X$_2$ | X$_3$-CH$_2$CH$_2$-phenyl | A | 1.00 | 378.5 |

TABLE 3-continued

Representative Compounds

| Cpd | R1 | R2 | R3 | Method* | LC RT | (M + H)+ |
|---|---|---|---|---|---|---|
| 3 | isobutyl-X₁ | X₂ (dashed) | X₃-CH₂-CH₂-phenyl | A | 1.76 | 344.4 |
| 4 | 4-NO₂-benzyl-X₁ | X₂ (dashed) | X₃-CH₂-CH₂-phenyl | A | 1.90 | 423.4 |
| 5 | 3,5-difluorobenzyl-X₁ | X₂ (dashed) | X₃-CH₂-CH₂-phenyl | A | 2.01 | 414.4 |
| 6 | benzyl-X₁ | 4-(O-C(O)-N(benzyl))-benzyl-X₂ | X₃-benzyl | A | 2.38 | 589.7 |
| 7 | benzyl-X₁ | 4-hydroxybenzyl-X₂ | X₃-CH₂-(3,5-bis(trifluoromethyl)phenyl) | A | 2.40 | 592.5 |
| 8 | benzyl-X₁ | 4-hydroxybenzyl-X₂ | X₃-CH₂-naphthyl | A | 2.20 | 506.6 |

TABLE 3-continued
Representative Compounds
| Cpd | R1 | R2 | R3 | Method* | LC RT | (M + H)+ |
|---|---|---|---|---|---|---|
| 9 | 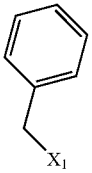 | 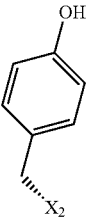 | 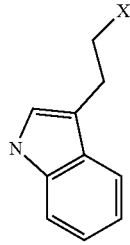 | A | 1.98 | 509.6 |
| 10 | 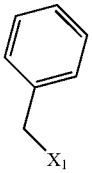 | 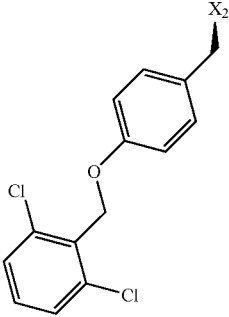 | 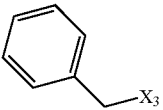 | A | 2.79 | 615.5 |
| 11 | 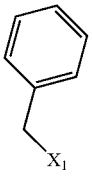 | 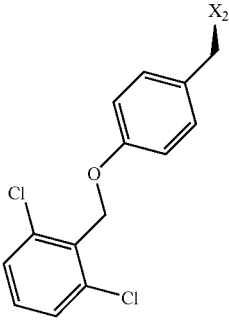 | 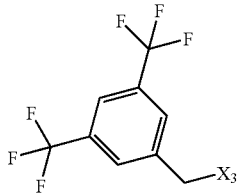 | A | 3.05 | 751.5 |
| 12 |  | 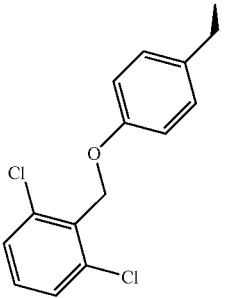 | 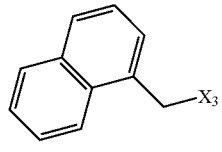 | A | 2.96 | 665.6 |

TABLE 3-continued

Representative Compounds

| Cpd | R1 | R2 | R3 | Method* | LC RT | (M + H)+ |
|---|---|---|---|---|---|---|
| 13 | Ph-CH2-X1 | 2,6-dichlorobenzyloxy-phenyl-CH2-X2 | indol-3-yl-CH2CH2-X3 | A | 2.75 | 668.6 |
| 14 | Ph-CH2-X1 | Ph-CH2-X2 | Ph-CH2-X3 | A | 2.35 | 440.5 |
| 15 | Ph-CH2-X1 | Ph-CH2-X2 | 3,5-bis(trifluoromethyl)benzyl-X3 | A | 2.70 | 576.5 |
| 16 | Ph-CH2-X1 | Ph-CH2-X2 | naphth-1-yl-CH2-X3 | A | 2.56 | 490.6 |
| 17 | Ph-CH2-X1 | Ph-CH(X2)- | indol-3-yl-CH2CH2-X3 | A | 2.06 | 493.6 |
| 18 | Ph-CH2-X1 | 3,5-bis(trifluoromethyl)benzyl-X2 | Ph-CH2-X3 | A | 2.62 | 576.5 |

TABLE 3-continued

Representative Compounds

| Cpd | R1 | R2 | R3 | Method* | LC RT | (M + H)+ |
|---|---|---|---|---|---|---|
| 19 | benzyl-X1 | 3,5-bis(trifluoromethyl)benzyl-X2 | 3,5-bis(trifluoromethyl)benzyl-X3 | A | 2.94 | 712.5 |
| 20 | benzyl-X1 | 3,5-bis(trifluoromethyl)benzyl-X2 | 1-naphthylmethyl-X3 | A | 2.77 | 626.6 |
| 21 | benzyl-X1 | 3,5-bis(trifluoromethyl)benzyl-X2 | X3-(2-(1H-indol-3-yl)ethyl) | A | 3.13 | 629.6 |
| 22 | benzyl-X1 | (1H-indol-3-yl)methyl-X2 | benzyl-X3 | A | 2.22 | 479.5 |
| 23 | benzyl-X1 | (1H-indol-3-yl)methyl-X2 | 3,5-bis(trifluoromethyl)benzyl-X3 | A | 2.58 | 615.5 |
| 24 | benzyl-X1 | (1H-indol-3-yl)methyl-X2 | 1-naphthylmethyl-X3 | A | 2.44 | 529.6 |

TABLE 3-continued
Representative Compounds
| Cpd | R1 | R2 | R3 | Method* | LC RT | (M + H)+ |
|---|---|---|---|---|---|---|
| 25 | 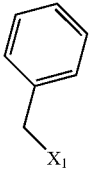 | 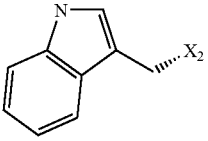 | 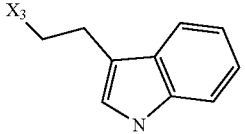 | A | 2.21 | 532.6 |
| 26 | 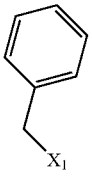 | 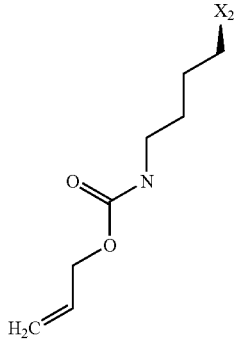 | 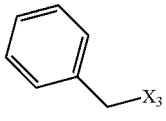 | A | 2.10 | 505.6 |
| 27 | 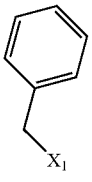 | 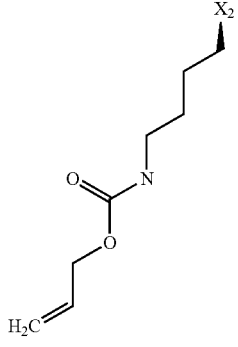 | 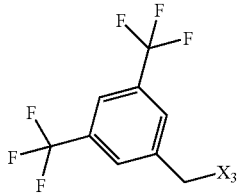 | A | 2.53 | 641.6 |
| 28 | 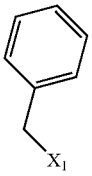 | 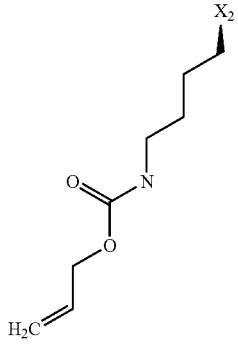 | 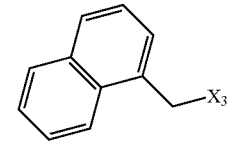 | A | 2.37 | 555.6 |

TABLE 3-continued

Representative Compounds

| Cpd | R1 | R2 | R3 | Method* | LC RT | (M + H)+ |
|---|---|---|---|---|---|---|
| 29 | benzyl-X₁ | X₂-(CH₂)₄-NH-C(O)-O-CH₂-CH=CH₂ | X₃-CH₂CH₂-(3-indolyl) | A | 2.13 | 558.6 |
| 30 | 3,5-bis(trifluoromethyl)benzyl-X₁ | 4-(X₂-CH₂)-phenyl-O-C(O)-N(benzyl) | benzyl-X₃ | A | 2.70 | 725.7 |
| 31 | 3,5-bis(trifluoromethyl)benzyl-X₁ | 4-hydroxy-benzyl-X₂ | X₃-CH₂-(1-naphthyl) | A | 2.55 | 642.6 |
| 32 | 3,5-bis(trifluoromethyl)benzyl-X₁ | 4-hydroxy-benzyl-X₂ | X₃-CH₂CH₂-(3-indolyl) | A | 2.40 | 645.6 |
| 33 | 3,5-bis(trifluoromethyl)benzyl-X₁ | 4-(X₂-CH₂)-phenyl-O-CH₂-(2,6-dichlorophenyl) | benzyl-X₃ | A | 3.05 | 751.5 |

TABLE 3-continued

Representative Compounds

| Cpd | R1 | R2 | R3 | Method* | LC RT | (M + H)+ |
|---|---|---|---|---|---|---|
| 34 | 3,5-bis(trifluoromethyl)benzyl-X₁ | 4-((2,6-dichlorobenzyl)oxy)benzyl-X₂ | naphthalen-1-ylmethyl-X₃ | A | 3.17 | 801.6 |
| 35 | 3,5-bis(trifluoromethyl)benzyl-X₁ | 4-((2,6-dichlorobenzyl)oxy)benzyl-X₂ | 2-(1H-indol-3-yl)ethyl-X₃ | A | 3.03 | 804.6 |
| 37 | 3,5-bis(trifluoromethyl)benzyl-X₁ | benzyl-X₂ | benzyl-X₃ | A | 2.69 | 576.5 |
| 36 | 3,5-bis(trifluoromethyl)benzyl-X₁ | benzyl-X₂ | 3,5-bis(trifluoromethyl)benzyl-X₃ | A | 2.99 | 712.5 |
| 37 | 3,5-bis(trifluoromethyl)benzyl-X₁ | benzyl-X₂ | naphthalen-1-ylmethyl-X₃ | A | 2.86 | 626.6 |

TABLE 3-continued

Representative Compounds

| Cpd | R1 | R2 | R3 | Method* | LC RT | (M + H)+ |
|---|---|---|---|---|---|---|
| 38 | 3,5-bis(trifluoromethyl)benzyl-X1 | benzyl-X2 | 2-(1H-indol-3-yl)ethyl-X3 | A | 2.68 | 629.6 |
| 39 | 3,5-bis(trifluoromethyl)benzyl-X1 | 3,5-bis(trifluoromethyl)benzyl-X2 | benzyl-X3 | A | 2.95 | 712.5 |
| 40 | 3,5-bis(trifluoromethyl)benzyl-X1 | 3,5-bis(trifluoromethyl)benzyl-X2 | naphthalen-1-ylmethyl-X3 | A | 3.07 | 762.6 |
| 41 | 3,5-bis(trifluoromethyl)benzyl-X1 | (1H-indol-3-yl)methyl-X2 | benzyl-X3 | A | 2.59 | 615.5 |
| 42 | 3,5-bis(trifluoromethyl)benzyl-X1 | (1H-indol-3-yl)methyl-X2 | 3,5-bis(trifluoromethyl)benzyl-X3 | A | 2.84 | 751.5 |
| 43 | 3,5-bis(trifluoromethyl)benzyl-X1 | (1H-indol-3-yl)methyl-X2 | naphthalen-1-ylmethyl-X3 | A | 2.78 | 665.6 |

TABLE 3-continued

Representative Compounds

| Cpd | R1 | R2 | R3 | Method* | LC RT | (M + H)+ |
|---|---|---|---|---|---|---|
| 44 | 3,5-bis(trifluoromethyl)benzyl-X1 | indol-3-ylmethyl-X2 | 2-(indol-3-yl)ethyl-X3 | A | 2.71 | 668.6 |
| 45 | 3,5-bis(trifluoromethyl)benzyl-X1 | allyl carbamate with butyl-X2 | benzyl-X3 | A | 2.51 | 641.6 |
| 46 | 3,5-bis(trifluoromethyl)benzyl-X1 | allyl carbamate with butyl-X2 | 3,5-bis(trifluoromethyl)benzyl-X3 | A | 2.79 | 777.6 |
| 47 | 3,5-bis(trifluoromethyl)benzyl-X1 | allyl carbamate with butyl-X2 | naphthalen-1-ylmethyl-X3 | A | 2.69 | 691.6 |

TABLE 3-continued

Representative Compounds

| Cpd | R1 | R2 | R3 | Method* | LC RT | (M + H)+ |
|---|---|---|---|---|---|---|
| 48 | 3,5-bis(trifluoromethyl)benzyl-X1 | allyloxycarbonylamino-butyl-X2 | 2-(1H-indol-3-yl)ethyl-X3 | A | 2.50 | 694.6 |
| 49 | isobutyl-X1 | 4-((benzylcarbamoyloxy)methyl)phenyl-X2 (via 4-CH2-X2) | benzyl-X3 | A | 2.35 | 555.6 |
| 50 | isobutyl-X1 | 4-(((3,5-bis(trifluoromethyl)benzyl)carbamoyloxy)methyl)phenyl-X2 | 3,5-bis(trifluoromethyl)benzyl-X3 | A | 2.89 | 827.6 |
| 51 | isobutyl-X1 | 4-hydroxy-benzyl-X2 | naphthalen-1-ylmethyl-X3 | A | 2.13 | 472.6 |

TABLE 3-continued

Representative Compounds

| Cpd | R1 | R2 | R3 | Method* | LC RT | (M + H)+ |
|---|---|---|---|---|---|---|
| 52 | H3C-CH(CH3)-CH2-X1 (isobutyl) | 4-hydroxybenzyl-X2 | 3-(2-ethyl)indolyl-X3 | A | 1.89 | 475.6 |
| 53 | H3C-CH(CH3)-CH2-X1 | 4-(2,6-dichlorobenzyloxy)benzyl-X2 | benzyl-X3 | A | 2.76 | 581.5 |
| 54 | H3C-CH(CH3)-CH2-X1 | 4-(2,6-dichlorobenzyloxy)benzyl-X2 | 3,5-bis(trifluoromethyl)benzyl-X3 | A | 3.03 | 717.5 |
| 55 | H3C-CH(CH3)-CH2-X1 | 4-(2,6-dichlorobenzyloxy)benzyl-X2 | 1-naphthylmethyl-X3 | A | 2.92 | 631.6 |

TABLE 3-continued

Representative Compounds

| Cpd | R1 | R2 | R3 | Method* | LC RT | (M + H)+ |
|---|---|---|---|---|---|---|
| 56 | isobutyl-X1 | 4-(2,6-dichlorobenzyloxy)benzyl-X2 | 3-(2-ethyl)indolyl-X3 | A | 2.71 | 634.6 |
| 57 | isobutyl-X1 | benzyl-X2 | benzyl-X3 | A | 2.26 | 406.5 |
| 58 | isobutyl-X1 | benzyl-X2 | 3,5-bis(trifluoromethyl)benzyl-X3 | A | 2.68 | 542.5 |
| 59 | isobutyl-X1 | benzyl-X2 | 1-naphthylmethyl-X3 | A | 2.50 | 456.6 |
| 60 | isobutyl-X1 | benzyl-X2 | 3-(2-ethyl)indolyl-X3 | A | 2.28 | 459.6 |
| 61 | isobutyl-X1 | 3,5-bis(trifluoromethyl)benzyl-X2 | benzyl-X3 | A | 2.60 | 542.5 |

TABLE 3-continued

Representative Compounds

| Cpd | R1 | R2 | R3 | Method* | LC RT | (M + H)+ |
|---|---|---|---|---|---|---|
| 62 | isobutyl-X₁ | 3,5-bis(trifluoromethyl)benzyl-X₂ | 3,5-bis(trifluoromethyl)benzyl-X₃ | A | 2.88 | 678.5 |
| 63 | isobutyl-X₁ | 3,5-bis(trifluoromethyl)benzyl-X₂ | 1-naphthylmethyl-X₃ | A | 2.82 | 592.5 |
| 64 | isobutyl-X₁ | 3,5-bis(trifluoromethyl)benzyl-X₂ | X₃-ethyl-indol-3-yl | A | 2.63 | 595.6 |
| 65 | isobutyl-X₁ | indol-3-ylmethyl-X₂ | benzyl-X₃ | A | 2.15 | 445.5 |
| 66 | isobutyl-X₁ | indol-3-ylmethyl-X₂ | 3,5-bis(trifluoromethyl)benzyl-X₃ | A | 2.56 | 581.5 |
| 67 | isobutyl-X₁ | indol-3-ylmethyl-X₂ | 1-naphthylmethyl-X₃ | A | 1.80 | 495.6 |

TABLE 3-continued

Representative Compounds

| Cpd | R1 | R2 | R3 | Method* | LC RT | (M + H)+ |
|---|---|---|---|---|---|---|
| 68 | H3C-CH(CH3)-CH2-X1 (isobutyl) | indol-3-ylmethyl-X2 | X3-CH2CH2-(indol-3-yl) | A | 2.14 | 498.6 |
| 69 | H3C-CH(CH3)-CH2-X1 | X2-(CH2)4-NH-C(O)-O-CH2-CH=CH2 | benzyl-X3 | A | 2.07 | 471.6 |
| 70 | H3C-CH(CH3)-CH2-X1 | X2-(CH2)4-NH-C(O)-O-CH2-CH=CH2 | 3,5-bis(trifluoromethyl)benzyl-X3 | A | 2.46 | 607.6 |
| 71 | H3C-CH(CH3)-CH2-X1 | X2-(CH2)4-NH-C(O)-O-CH2-CH=CH2 | naphth-1-ylmethyl-X3 | A | 2.28 | 521.6 |
| 72 | H3C-CH(CH3)-CH2-X1 | H2C=CH-CH2-O-C(O)-NH-(CH2)4-X2 | X3-CH2CH2-(indol-3-yl) | A | 2.06 | 524.6 |

TABLE 3-continued

Representative Compounds

| Cpd | R1 | R2 | R3 | Method* | LC RT | (M + H)+ |
|---|---|---|---|---|---|---|
| 73 | H2C=CHCH2-O-C(O)-NH-(CH2)4-X1 | 4-HO-C6H4-CH2-X2 | PhCH2-X3 | A | 1.82 | 521.6 |
| 74 | H2C=CHCH2-O-C(O)-NH-(CH2)4-X1 | 4-HO-C6H4-CH2-X2 | 3,5-(CF3)2-C6H3-CH2-X3 | A | 2.20 | 657.6 |
| 75 | H2C=CHCH2-O-C(O)-NH-(CH2)4-X1 | 4-HO-C6H4-CH2-X2 | 1-naphthyl-CH2-X3 | A | 2.04 | 571.6 |
| 76 | H2C=CHCH2-O-C(O)-NH-(CH2)4-X1 | 4-HO-C6H4-CH(X2)- | 3-indolyl-CH2CH2-X3 | A | 1.84 | 574.6 |
| 77 | H2C=CHCH2-O-C(O)-NH-(CH2)4-X1 | 2,6-Cl2-C6H3-CH2-O-C6H4-CH2-X2 | PhCH2-X3 | A | 2.59 | 680.6 |

TABLE 3-continued

Representative Compounds

| Cpd | R1 | R2 | R3 | Method* | LC RT | (M + H)+ |
|---|---|---|---|---|---|---|
| 78 | H2C=CHCH2-O-C(O)-NH-(CH2)4-X1 (allyl carbamate of butyl-X1) | 4-(2,6-dichlorobenzyloxy)benzyl-X2 | 3,5-bis(trifluoromethyl)benzyl-X3 | A | 2.87 | 816.6 |
| 79 | H2C=CHCH2-O-C(O)-NH-(CH2)4-X1 | 4-(2,6-dichlorobenzyloxy)benzyl-X2 | naphthalen-1-ylmethyl-X3 | A | 2.76 | 730.7 |
| 80 | H2C=CHCH2-O-C(O)-NH-(CH2)4-X1 | 4-(2,6-dichlorobenzyloxy)benzyl-X2 | 2-(1H-indol-3-yl)ethyl-X3 | A | 2.54 | 733.7 |
| 81 | H2C=CHCH2-O-C(O)-NH-(CH2)4-X1 | benzyl-X2 | benzyl-X3 | A | 2.13 | 505.6 |
| 82 | H2C=CHCH2-O-C(O)-NH-(CH2)4-X1 | benzyl-X2 | 3,5-bis(trifluoromethyl)benzyl-X3 | A | 2.51 | 641.6 |

TABLE 3-continued

Representative Compounds

| Cpd | R1 | R2 | R3 | Method* | LC RT | (M + H)+ |
|---|---|---|---|---|---|---|
| 83 | allyl carbamate-(CH2)4-X1 | benzyl-X2 | 1-naphthylmethyl-X3 | A | 2.44 | 555.6 |
| 84 | allyl carbamate-(CH2)4-X1 | benzyl-X2 | X3-(CH2)2-(3-indolyl) | A | 2.65 | 558.6 |
| 85 | allyl carbamate-(CH2)4-X1 | 3,5-bis(trifluoromethyl)benzyl-X2 | benzyl-X3 | A | 2.46 | 641.6 |
| 86 | allyl carbamate-(CH2)4-X1 | 3,5-bis(trifluoromethyl)benzyl-X2 | 3,5-bis(trifluoromethyl)benzyl-X3 | A | 2.77 | 777.6 |
| 87 | allyl carbamate-(CH2)4-X1 | 3,5-bis(trifluoromethyl)benzyl-X2 | 1-naphthylmethyl-X3 | A | 2.67 | 691.6 |

TABLE 3-continued

Representative Compounds

| Cpd | R1 | R2 | R3 | Method* | LC RT | (M + H)+ |
|---|---|---|---|---|---|---|
| 88 | allyl O-C(O)-NH-(CH2)4-X1 | 3,5-bis(trifluoromethyl)benzyl-X2 | 3-(2-ethyl)indole-X3 | A | 2.48 | 694.6 |
| 89 | allyl O-C(O)-NH-(CH2)4-X1 | indol-3-ylmethyl-X2 | benzyl-X3 | A | 2.06 | 544.6 |
| 90 | allyl O-C(O)-NH-(CH2)4-X1 | indol-3-ylmethyl-X2 | 3,5-bis(trifluoromethyl)benzyl-X3 | A | 2.46 | 680.6 |
| 91 | allyl O-C(O)-NH-(CH2)4-X1 | indol-3-ylmethyl-X2 | naphth-1-ylmethyl-X3 | A | 2.29 | 594.7 |
| 92 | allyl O-C(O)-NH-(CH2)4-X1 | indol-3-ylmethyl-X2 | 3-(2-ethyl)indole-X3 | A | 2.07 | 597.7 |

TABLE 3-continued

Representative Compounds

| Cpd | R1 | R2 | R3 | Method* | LC RT | (M + H)⁺ |
|---|---|---|---|---|---|---|
| 93 | H₂C=CH-CH₂-O-C(=O)-NH-(CH₂)₄-X₁ (allyloxycarbonylamino-butyl) | X₂-(CH₂)₄-NH-C(=O)-O-CH₂-CH=CH₂ | benzyl-X₃ | A | 1.97 | 570.7 |
| 94 | H₂C=CH-CH₂-O-C(=O)-NH-(CH₂)₄-X₁ | X₂-(CH₂)₄-NH-C(=O)-O-CH₂-CH=CH₂ | 3,5-bis(trifluoromethyl)benzyl-X₃ | A | 2.38 | 706.6 |
| 95 | H₂C=CH-CH₂-O-C(=O)-NH-(CH₂)₄-X₁ | X₂-(CH₂)₄-NH-C(=O)-O-CH₂-CH=CH₂ | 1-naphthylmethyl-X₃ | A | 2.21 | 620.7 |
| 96 | H₂C=CH-CH₂-O-C(=O)-NH-(CH₂)₄-X₁ | H₂C=CH-CH₂-O-C(=O)-NH-(CH₂)₃-X₂ | X₃-CH₂-CH₂-(3-indolyl) | A | 1.99 | 623.7 |
| 97 | HOOC-CH₂-X₁ | X₂ | X₃-CH₂-CH₂-phenyl | B | 1.92 | 346.4 |

TABLE 3-continued

Representative Compounds

| Cpd | R1 | R2 | R3 | Method* | LC RT | (M + H)+ |
|---|---|---|---|---|---|---|
| 98 | 4-nitrobenzyl ester-CH2-X1 | X2······ | X3-CH2CH2-phenyl | B | 1.99 | 481.5 |
| 99 | 3,5-difluorobenzyl-X1 | X2······ | X3-CH2CH2-phenyl | B | 2.04 | 414.5 |
| 100 | 3-nitrobenzyl-X1 | X2······ | X3-CH2CH2-phenyl | B | 1.94 | 464.5^ |
| 101 | 4-nitrobenzyl-X1 | X2······ | X3-CH2CH2-phenyl | B | 1.93 | 464.5^ |

*All compounds synthesized using Method A result in diastereo-mixture of two compounds. The synthesis results in both alpha and beta configuration of the proton at the carbon bridge-head as shown in Example 4.
^MS is acetonitrile adduct [M + CH₃CN + 1]+.

Example 4

The Synthesis of Representative Reverse-Turn Mimetic

This example illustrates the synthesis of further representative reverse-turn mimetics of this invention.

Compound 1

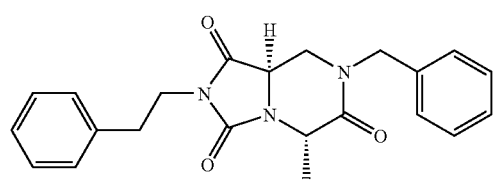

The diastereo-mixture containing compound 1 and 2 (TABLE 3) was synthesized according to the Method A using appropriate $R^1$, $R^2$ and $R^3$ components. Compound 1 was purified by RP-HPLC (C-18 semi-preparative, 7 um, 7.8×300 mm): 30% isocratic ACN (0.1% TFA) for 5 min followed by 30-50% ACN/H20 (0.1% TFA) gradient for 30 min at 4 ml/min, $t_R$: 30.59 min. ¹H NMR was carried out on HPLC purified products of this mimetic and spectra were assigned by combination of 1D and 2D DQFCOSY, TCOSY, and ROESY experiments. All spectra were consistent with the structure indicated above for compounds 1 (TABLE 3). ¹H NMR (500 MHz, CDCl₃, −20 C, ppm, Compound 1): δ 7.38-7.34 (3H, m, ArH), 7.25-7.16 (7H, m, ArH), 4.65-4.56 (3H, m), 4.14 (1H, q, J=6.5, 6.0 Hz), 3.78-3.66 (2H, oct), 3.47 (1H, dd, J=4.5, 12.0 Hz), 3.035 (1H, t, J=11.5 Hz), 2.90 (2H, t, J=7.5 Hz), 1.56 (3H, d, J=7.0 Hz). MS(ES+): m/z 378.5 [M+H]+.

Compound 2

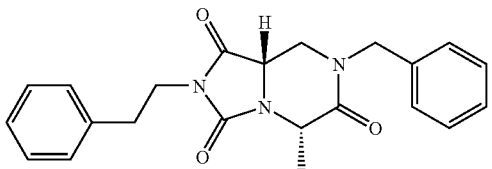

The diastereo mixture containing compound 1 and 2 (TABLE 3) was synthesized according to the Method A using appropriate $R^1$, $R^2$ and $R^3$ components. Compound 2 was purified by RP-HPLC (C-18 semi-preparative, 7 um, 7.8×300 mm): 30% isocratic ACN (0.1% TFA) for 5 min followed by 30-50% ACN/H20 (0.1% TFA) gradient for 30 min at 4 ml/min, $t_R$: 31.57 min. $^1$H NMR was carried out on HPLC purified products of this mimetic and spectra were assigned by combination of 1D and 2D DQFCOSY, TCOSY, and ROESY experiments. All spectra were consistent with the structure indicated above for compounds 2. $^1$H NMR (500 MHz, CDCl$_3$, −20 C, ppm): δ 7.38-7.33 (3H, m, ArH), 7.25-7.15(7H, m, ArH), 4.64 (2H, dd, J=14.5, J=15.0 Hz), 4.36 (1H, q, J=7.0 Hz), 4.01 (1H, dd, J=3.5, 4.5 Hz), 3.76-3.66 (2H, m), 3.48 (1H, dd, J=4.0, J=3.5 Hz), 3.08 (1H, t, J=11.5 Hz), 2.95-2.86 (2H, m), 1.77 (3H, d, J=7.0 Hz). MS(ES+): m/z 378.5 [M+H]$^+$.

Example 5

Integrin Biological Activity of Representative Compounds

An assay measuring the ability of the compounds of Example 3 to antagonize binding of CS1 peptide to $\alpha_4\beta_1$ integrin was performed. A modification of the procedure of Vanderslice, P. et al. (*J. Immunol.*, 1997, 1710-1718) (incorporated herein by reference) was utilized.

In brief, 100 μL/well of a solution of biotinylated CS1 peptide (1 mg/100 mL of phosphate buffered saline (PBS)) was incubated in a NeutrAvidin plate (Pierce) for 1 h at room temperature. The plate was then washed 3× with distilled water and treated with 200 μL of blocking buffer (3% BSA in PBS) for at least 4 h. Blocked plates were washed as above. Harvested Ramos cells (10$^7$/mL) were resuspended in PBS containing 10 μL of calcein AM/mL and incubated 30 min in the dark. This suspension was diluted with 45 mL PBS and the cells harvested by centrifugation and aspiration. The cells were resuspended in binding buffer (~5×10$^5$/mL). If cell lysis was to be monitored ethidium homodimer was added to the buffer to a final concentration of 5 μM. A solution (10 μL) of compound to be tested or control peptide was added to appropriate wells followed by 90 μL of the cell suspension. The plate was incubated at 37° C. for 1 h. When ethidium homodimer was added, fluorescence at 535/617 nm was measured before rinsing. Otherwise, the plate was washed 3×, 50 μL of lysis buffer was added to each well, the plate rocked in the dark for 10 min, and the fluorescence monitored at 485 nm excitation and 535 nm emission.

Preferably, the compounds of this invention have an inhibition value of better than or equal to 20% at 2 μM concentration in this assay. To this end, preferred compounds of this invention are compounds 16-18, 20, 24, 31-35, 49, 85, 86, 94 and 95. As such, the compounds of this invention effectively inhibit cell adhesion and possess activity as anti-inflammatory agents.

Example 6

Tachykinin Antagonism Assay of Representative Compounds

The compounds of this invention are useful for antagonizing tachykinins, in particular substance P in the treatment of inflammatory diseases, central nervous system disorders, gastrointestinal disorders, pain or migraine and asthma in a mammal in need of such treatment. This activity can be demonstrated by the following assay.

An assay measuring the ability of the compounds of Example 3 to antagonize binding of substance P peptide to its receptor neurokinin-1 was performed. Substance P is known to act upon cells via the mobilization of calcium (Bordey et al., *Glia* 11: 277-283, 1994). The compounds were assessed for their ability to inhibit the action of Substance P with the use of a Fluorescent Imaging Plate Reader (FLIPR) from Molecular Devices (Shroeder et al., *J. Biomol. Screening* 1: 75-80, 1996; U.S. Pat. Nos. 5,112,134; 4,968,148). U373 MG cells, which endogenously express the neurokinin-1 receptor for Substance P, were obtained from the American Type Culture Collection and grown to confluence in 96-well plates in modified Eagle's minimum essential medium (MEM) with 10% fetal bovine serum, 1 mM sodium pyruvate, 2mM L-glutamine, and 1 mM non-essential amino acids in a humidified incubator at 37° C. and 5% CO$_2$/95% filtered air. The cells were stained with Calcium Indicator dye from Molecular Devices for thirty minutes at room temperature; compounds were added to the cells, and the cells were further incubated for twenty minutes. This dye is similar to Fluo-3, Fluo-4, and Calcium Green dyes used by other researchers (Lin et al., *Biotechniques* 26: 318-326, 1999) in that it increases in fluorescence in the presence of calcium; the Molecular Devices version is preferable because the cells need not be washed following staining with the dye. Dye was made fresh on the day of the assay and included 2.5 mM probenecid, an anion exchange inhibitor which helps to keep the dye retained by the cells. Substance P was added in Hank's salt solution with 1% BSA to give a final concentration of 1 mM and the resultant change in fluorescence intensity was monitored for thirty seconds with an excitation wavelength of 480 nm and an emission of 515 nm. Some wells were maintained as controls that were not incubated with any compound, and the peak fluorescence readings resulting from the wells which received compounds were compared to these control wells in order to determine the degree of inhibition.

Preferably, the compounds of this invention have an inhibition value of better than or equal to 50% at 5 μM concentration in this assay. To this end, preferred compounds of this invention are compounds 15, 23, 50, 58, 63, 74, 81-83, 89-91 and 95. As such, the compounds of this invention effectively inhibit binding of substance P peptide to its receptor neurokinin-1 and are effective in the treatment of inflammatory diseases and central nervous system disorders.

It will be appreciated that, although specific embodiments of the invention have been described herein for the purposes of illustration, various modifications may be made without departing from the spirit and scope of the invention. Accordingly, the invention is not limited except by the appended claims.

We claim:

1. A method of antagonizing the binding of $\alpha_4\beta_1$ integrin to its cognate extracellular matrix receptors in a mammal, comprising administering to said mammal an effective amount of a compound having the structure:

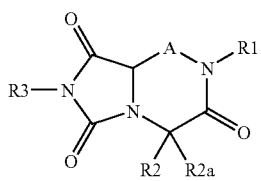

or a pharmaceutically acceptable salt or stereoisomer thereof, wherein

A is —(CR$_4$R$_{4a}$)$_m$— where m is 1, 2 or 3;

R$_2$ and R$_4$ are, at each occurrence, the same or different and independently an amino acid side chain moiety or amino acid side chain derivative;

R$_{2a}$ and R$_{4a}$ are, at each occurrence, the same or different and independently hydrogen, hydroxy, —COOH, —CONH$_2$, —R$_5$, —OR$_5$, —COOR$_5$, —COR$_5$ or —CONHR$_5$, where R$_5$ is lower alkyl optionally substituted with halogen or hydroxy; and R$_1$ and R$_3$ are the same or different and independently an amino acid, an amino acid side chain moiety, an amino acid side chain derivative, a peptide, a peptide derivative, a solid support, or a protein;

wherein said method is used to treat a condition associated with excessive α$_4$β$_1$ integrin-mediated cell adhesion in a mammal in need of such treatment, and said condition is treated by a reduction in the binding of α$_4$β$_1$ integrin to its cognate extracellular matrix receptors; and wherein said condition is multiple sclerosis, allergic airway response, metastatic melanoma, rheumatoid arthritis, asthma, diabetes, or inflammatory bowel disease.

2. The method of claim 1, wherein said condition is multiple sclerosis.

3. The method of claim 1, wherein the condition to be treated is rheumatoid arthritis.

4. The method of claim 1, wherein the condition to be treated is asthma.

5. The method of claim 1, wherein the condition to be treated is inflammatory bowel disease.

6. A method of antagonizing the binding of substance P to the neurokinin-1 receptor in a mammal, comprising administering to a mammal an effective amount of a compound having the structure:

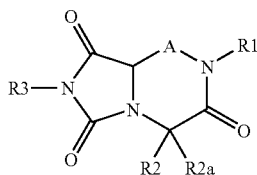

or a pharmaceutically acceptable salt or stereoisomer thereof, wherein

A is —(CR$_4$R$_{4a}$)$_m$— where m is 1, 2 or 3;

R$_2$ and R$_4$ are, at each occurrence, the same or different and independently an amino acid side chain moiety or amino acid side chain derivative;

R$_{2a}$ and R$_{4a}$ are, at each occurrence, the same or different and independently hydrogen, hydroxy, —COOH, —CONH$_2$, —R$_5$, —OR$_5$, —COOR$_5$, —COR$_5$ or —CONHR$_5$, where R$_5$ is lower alkyl optionally substituted with halogen or hydroxy; and R$_1$ and R$_3$ are the same or different and independently an amino acid, an amino acid side chain moiety, an amino acid side chain derivative, a peptide, a peptide derivative, a solid support, or a protein;

wherein said method is used to treat a condition responsive to a reduction of substance P activity in a mammal in need of such treatment; and wherein said condition is emesis, pain, migraine, oedema, rheumatoid arthritis, asthma, bronchial hyperactivity, allergic rhinitis, ulcerative colitis, Crohn's disease, proliferative vitreoretinopathy, irritable bowel syndrome, cystitis, bladder detruser hyperreflexia, anxiety, depression, dysthymic disorders, chronic obstructive airway disease, neuropathy, contact dermatitis, atopic dermatitis, urticaria or eczematoid dermatitis.

7. The method of claim 6, wherein the condition is migraine.

8. The method of claim 6, wherein the condition is rheumatoid arthritis.

9. The method of claim 6, wherein the condition is asthma, bronchial hyperactivity, or allergic rhinitis.

10. The method of claim 6, wherein the condition is Crohn's disease or irritable bowel syndrome.

11. The method of claim 6, wherein the condition is anxiety, depression, or dysthymic disorders.

12. The method of claim 6, wherein the condition is chronic obstructive airway disease.

13. The method of claim 6, wherein the condition is contact dermatitis, atopic dermatitis, urticaria or eczematoid dermatitis.

* * * * *